(12) United States Patent
Comenencia Ortiz et al.

(10) Patent No.: US 12,257,014 B2
(45) Date of Patent: Mar. 25, 2025

(54) DEVICES AND METHODS FOR CRIMP INTERFACE FOR CABLE TENSION SENSOR

(71) Applicant: Intuitive Surgical Operations, Inc., Sunnyvale, CA (US)

(72) Inventors: Lizmarie Comenencia Ortiz, Sunnyvale, CA (US); Jason Miao, Sunnyvale, CA (US); David Moreira Ridsdale, Saratoga, CA (US); Harsukhdeep S. Ratia, Foster City, CA (US); Sharathchandra Somayaji, Santa Clara, CA (US); Zhou Ye, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 206 days.

(21) Appl. No.: 17/840,859

(22) Filed: Jun. 15, 2022

(65) Prior Publication Data

US 2022/0401171 A1 Dec. 22, 2022

Related U.S. Application Data

(60) Provisional application No. 63/213,369, filed on Jun. 22, 2021.

(51) Int. Cl.
*A61B 34/00* (2016.01)
*A61B 34/35* (2016.01)
(Continued)

(52) U.S. Cl.
CPC ............ *A61B 34/71* (2016.02); *A61B 34/35* (2016.02); *G01L 1/22* (2013.01); *G01L 5/10* (2013.01); *A61B 2034/715* (2016.02)

(58) Field of Classification Search
None
See application file for complete search history.

(56) References Cited

U.S. PATENT DOCUMENTS

| | | |
|---|---|---|
| 4,860,742 A | 8/1989 | Park et al. |
| 4,906,907 A | 3/1990 | Tsuchihashi et al. |

(Continued)

FOREIGN PATENT DOCUMENTS

| | | |
|---|---|---|
| CA | 2709634 A1 | 7/2009 |
| DE | 1147411 B | 4/1963 |

(Continued)

OTHER PUBLICATIONS

Cepolina F. et al., "Review of robotic fixtures for minimally invasive surgery," International Journal of Medical Robotics and Computer Assisted Surgery, 2004, pp. 43-63, vol. 1, Issue-1.

(Continued)

*Primary Examiner* — Peter J Macchiarolo
*Assistant Examiner* — Jermaine L Jenkins

(57) ABSTRACT

A medical device comprises an end effector, a mechanical structure, a connector, and a force sensor unit. The connector extends from a drive component of the mechanical structure to the end effector. Motion of the drive component produces a tension force within the connector, which is associated with an end effector torque or force exerted by the end effector. The force sensor unit comprises a body, and the body is coupled in-line with the connector so that strain in the connector is imparted to the body. A strain sensor measures the strain on the body as an indication of strain in the connector, which is an indication of torque or force at the end effector. The connector may be continuous, and coupled to the body with a slack relief portion of the connector within the body. Alternatively, the connector may be discontinuous and coupled to opposite ends of the body.

21 Claims, 19 Drawing Sheets

(51) Int. Cl.
  *G01L 1/22* (2006.01)
  *G01L 5/10* (2020.01)

(56) References Cited

U.S. PATENT DOCUMENTS

| | | | |
|---|---|---|---|
| 5,624,398 A | 4/1997 | Smith et al. |
| 5,625,576 A | 4/1997 | Massie et al. |
| 5,784,542 A | 7/1998 | Ohm et al. |
| 5,855,583 A | 1/1999 | Wang et al. |
| 6,197,017 B1 | 3/2001 | Brock et al. |
| 6,331,181 B1 | 12/2001 | Tierney et al. |
| 6,394,998 B1 | 5/2002 | Wallace et al. |
| 6,459,926 B1 | 10/2002 | Nowlin et al. |
| 6,494,882 B1 | 12/2002 | Lebouitz et al. |
| 6,594,552 B1 | 7/2003 | Nowlin et al. |
| 6,817,974 B2 | 11/2004 | Cooper et al. |
| 6,879,880 B2 | 4/2005 | Nowlin et al. |
| 6,994,708 B2 | 2/2006 | Manzo |
| 7,083,571 B2 | 8/2006 | Wang et al. |
| 7,169,141 B2 | 1/2007 | Brock et al. |
| 7,935,130 B2 | 5/2011 | Williams |
| 8,004,229 B2 | 8/2011 | Nowlin et al. |
| 8,306,656 B1 | 11/2012 | Schaible et al. |
| 8,375,808 B2 | 2/2013 | Blumenkranz et al. |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,551,115 B2 | 10/2013 | Steger et al. |
| 8,602,288 B2 | 12/2013 | Shelton, IV et al. |
| 8,613,230 B2 | 12/2013 | Blumenkranz et al. |
| 8,620,473 B2 | 12/2013 | Diolaiti et al. |
| 8,628,518 B2 | 1/2014 | Blumenkranz et al. |
| 8,771,270 B2 | 7/2014 | Burbank |
| 8,800,838 B2 | 8/2014 | Shelton, IV |
| 8,945,095 B2 | 2/2015 | Blumenkranz et al. |
| 9,028,494 B2 | 5/2015 | Shelton, IV et al. |
| 9,192,448 B2 | 11/2015 | Blumenkranz |
| 9,204,923 B2 | 12/2015 | Manzo et al. |
| 9,232,979 B2 | 1/2016 | Parihar et al. |
| 9,358,682 B2* | 6/2016 | Ruiz Morales ........ A61B 34/77 |
| 9,671,860 B2 | 6/2017 | Ogawa et al. |
| 9,707,684 B2 | 7/2017 | Ruiz et al. |
| 9,782,214 B2 | 10/2017 | Houser et al. |
| 9,943,375 B2 | 4/2018 | Blumenkranz et al. |
| 9,952,107 B2 | 4/2018 | Blumenkranz et al. |
| 10,085,809 B2 | 10/2018 | Blumenkranz et al. |
| 10,130,366 B2 | 11/2018 | Shelton, IV et al. |
| 10,201,365 B2 | 2/2019 | Boudreaux et al. |
| 10,219,874 B2 | 3/2019 | Yu et al. |
| 10,238,458 B2 | 3/2019 | Verner et al. |
| 10,363,107 B2 | 7/2019 | Blumenkranz et al. |
| 10,398,433 B2 | 9/2019 | Boudreaux et al. |
| 10,595,836 B2 | 3/2020 | Smaby et al. |
| 10,595,887 B2 | 3/2020 | Shelton, IV et al. |
| 10,653,435 B2 | 5/2020 | Shelton, IV et al. |
| 10,682,141 B2 | 6/2020 | Moore et al. |
| 11,020,138 B2* | 6/2021 | Ragosta ............... A61B 34/71 |
| 11,079,292 B2 | 8/2021 | Lisiak |
| 11,369,411 B2* | 6/2022 | Page ................... A61B 17/34 |
| 2003/0135203 A1 | 7/2003 | Wang et al. |
| 2005/0096502 A1 | 5/2005 | Khalili |
| 2005/0119527 A1 | 6/2005 | Banik et al. |
| 2005/0200324 A1 | 9/2005 | Guthart et al. |
| 2007/0018958 A1 | 1/2007 | Tavakoli et al. |
| 2007/0043338 A1 | 2/2007 | Moll et al. |
| 2007/0078484 A1 | 4/2007 | Talarico et al. |
| 2007/0119274 A1 | 5/2007 | Devengenzo et al. |
| 2007/0156019 A1 | 7/2007 | Larkin et al. |
| 2008/0046122 A1 | 2/2008 | Manzo et al. |
| 2008/0065105 A1 | 3/2008 | Larkin et al. |
| 2008/0132893 A1 | 6/2008 | D'Amelio et al. |
| 2008/0147090 A1 | 6/2008 | Seibold et al. |
| 2009/0088774 A1 | 4/2009 | Swarup et al. |
| 2009/0088775 A1 | 4/2009 | Swarup et al. |
| 2009/0324161 A1 | 12/2009 | Prisco |
| 2010/0063478 A1 | 3/2010 | Selkee |
| 2010/0219388 A1 | 9/2010 | Schena |
| 2010/0313679 A1 | 12/2010 | Larkin et al. |
| 2011/0015632 A1 | 1/2011 | Artale |
| 2011/0046659 A1 | 2/2011 | Ramstein et al. |
| 2011/0071543 A1 | 3/2011 | Prisco et al. |
| 2011/0277775 A1 | 11/2011 | Holop et al. |
| 2011/0282356 A1 | 11/2011 | Solomon et al. |
| 2011/0295269 A1 | 12/2011 | Swensgard et al. |
| 2011/0295270 A1 | 12/2011 | Giordano et al. |
| 2012/0116391 A1 | 5/2012 | Houser et al. |
| 2012/0123441 A1 | 5/2012 | Au et al. |
| 2013/0291654 A1 | 11/2013 | Blumenkranz et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0052150 A1 | 2/2014 | Taylor et al. |
| 2014/0088614 A1 | 3/2014 | Blumenkranz |
| 2014/0107627 A1 | 4/2014 | Blumenkranz et al. |
| 2014/0257333 A1 | 9/2014 | Blumenkranz |
| 2015/0135832 A1 | 5/2015 | Blumenkranz et al. |
| 2015/0150635 A1 | 6/2015 | Kilroy et al. |
| 2015/0164598 A1 | 6/2015 | Blumenkranz et al. |
| 2015/0374447 A1 | 12/2015 | Blumenkranz et al. |
| 2017/0007345 A1 | 1/2017 | Smith et al. |
| 2017/0165017 A1 | 6/2017 | Chaplin et al. |
| 2017/0172687 A1 | 6/2017 | Smith et al. |
| 2017/0215944 A1 | 8/2017 | Keffeler |
| 2017/0303996 A1 | 10/2017 | Kerr et al. |
| 2018/0042689 A1 | 2/2018 | Mozdzierz et al. |
| 2018/0078249 A1 | 3/2018 | Stoy et al. |
| 2018/0296285 A1* | 10/2018 | Simi ..................... B25J 3/04 |
| 2019/0069966 A1 | 3/2019 | Petersen et al. |
| 2019/0094084 A1* | 3/2019 | Swinehart ............ G01L 1/02 |
| 2019/0125354 A1 | 5/2019 | Deck et al. |
| 2019/0175188 A1 | 6/2019 | Mohan |
| 2019/0175887 A1 | 6/2019 | Shameli |
| 2019/0201018 A1 | 7/2019 | Shelton, IV et al. |
| 2019/0223960 A1 | 7/2019 | Chaplin et al. |
| 2019/0223966 A1 | 7/2019 | Holop et al. |
| 2019/0336228 A1 | 11/2019 | Blumenkranz et al. |
| 2020/0253669 A1 | 8/2020 | Diolaiti et al. |
| 2020/0278265 A1 | 9/2020 | Suresh |
| 2020/0397502 A1* | 12/2020 | Crews ................... A61B 34/30 |
| 2021/0022819 A1 | 1/2021 | Duque et al. |
| 2021/0045819 A1 | 2/2021 | Castillo et al. |
| 2021/0181048 A1 | 6/2021 | Lisiak |
| 2024/0130812 A1* | 4/2024 | Suresh ................. A61B 34/35 |

FOREIGN PATENT DOCUMENTS

| | | | |
|---|---|---|---|
| EP | 0590713 A2 | 4/1994 |
| EP | 2362285 A2 | 8/2011 |
| EP | 2431000 A2 | 3/2012 |
| JP | 9318469 A | 12/1997 |
| JP | 2002159509 A | 6/2002 |
| KR | 100778387 B1 | 11/2007 |
| WO | WO-2007143859 A1 | 12/2007 |
| WO | WO-2009123891 A1 | 10/2009 |
| WO | WO-2012166806 A1 | 12/2012 |
| WO | WO-2014151952 A1 | 9/2014 |
| WO | WO-2014172213 A2 | 10/2014 |
| WO | WO-2017064303 A1 | 4/2017 |
| WO | WO-2020102774 A1 | 5/2020 |
| WO | WO-2020102776 A1 | 5/2020 |
| WO | WO-2020102778 A1 | 5/2020 |
| WO | WO-2020102780 A1 | 5/2020 |
| WO | WO-2021076765 A1 | 4/2021 |
| WO | WO-2021097386 A1 | 5/2021 |

OTHER PUBLICATIONS

Hazel D., "Comparing Strain Gage Measurements to Force Calculations in a Simple Cantilever Beam," Worcester Polytechnic Institute Major Qualifying Project, Jan. 27, 2016, 39 pages.

Mertmann M., et al., "Grippers for the Micro Assembly Containing Shape Memory Actuators and Sensors," Le Journal de Physique IV

(56) References Cited

OTHER PUBLICATIONS

France 7 (1997), Conference C5, Supplement of Journal de Physique III of Nov. 1997, pp. C5-621-C5-626.
Seibold, Ulrich et al., "A 6-Axis force/torque sensor design for haptic feedback in minimally invasive robotic surgery." In: Proceedings of the 2nd VDE World Microtechnologies, 2003, 6 Pages.
Vertut, J, and Coiffet, P., "Robot Technology: Teleoperation and Robotics Evolution and Development." English translation, Prentice-Hall, Inc., Inglewood Cliffs, NJ, USA 1986, vol. 3A, 332 pages.

\* cited by examiner

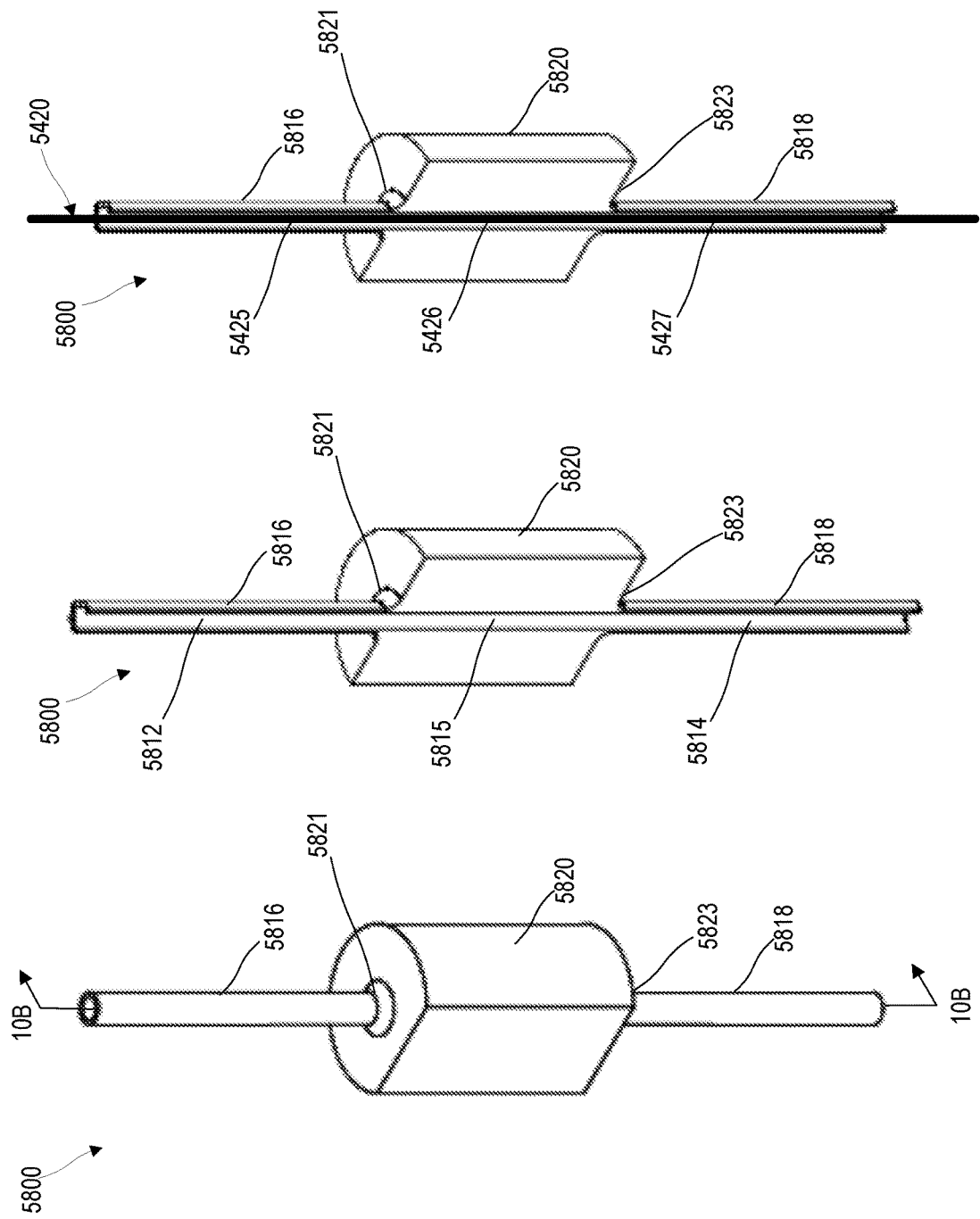

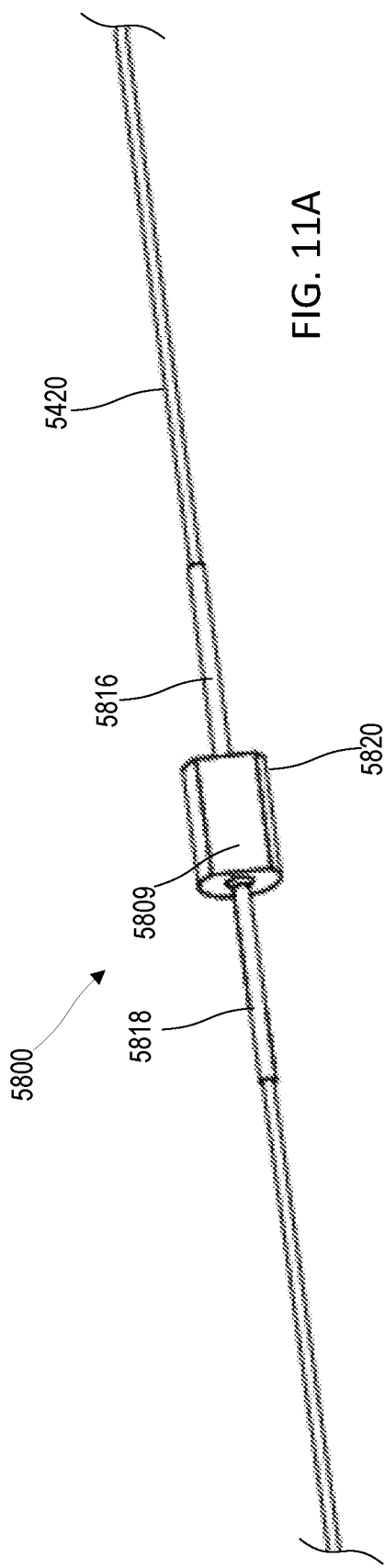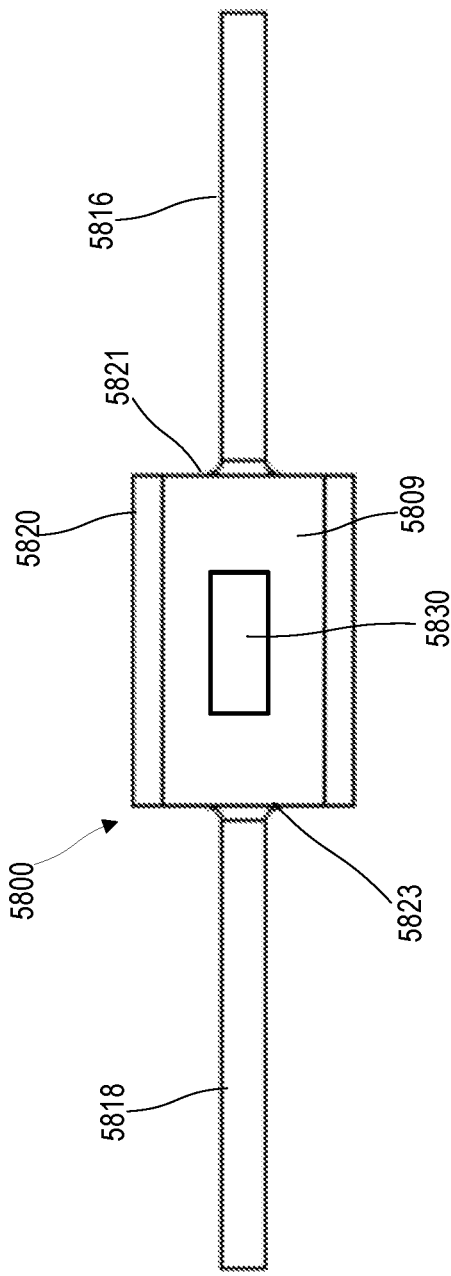

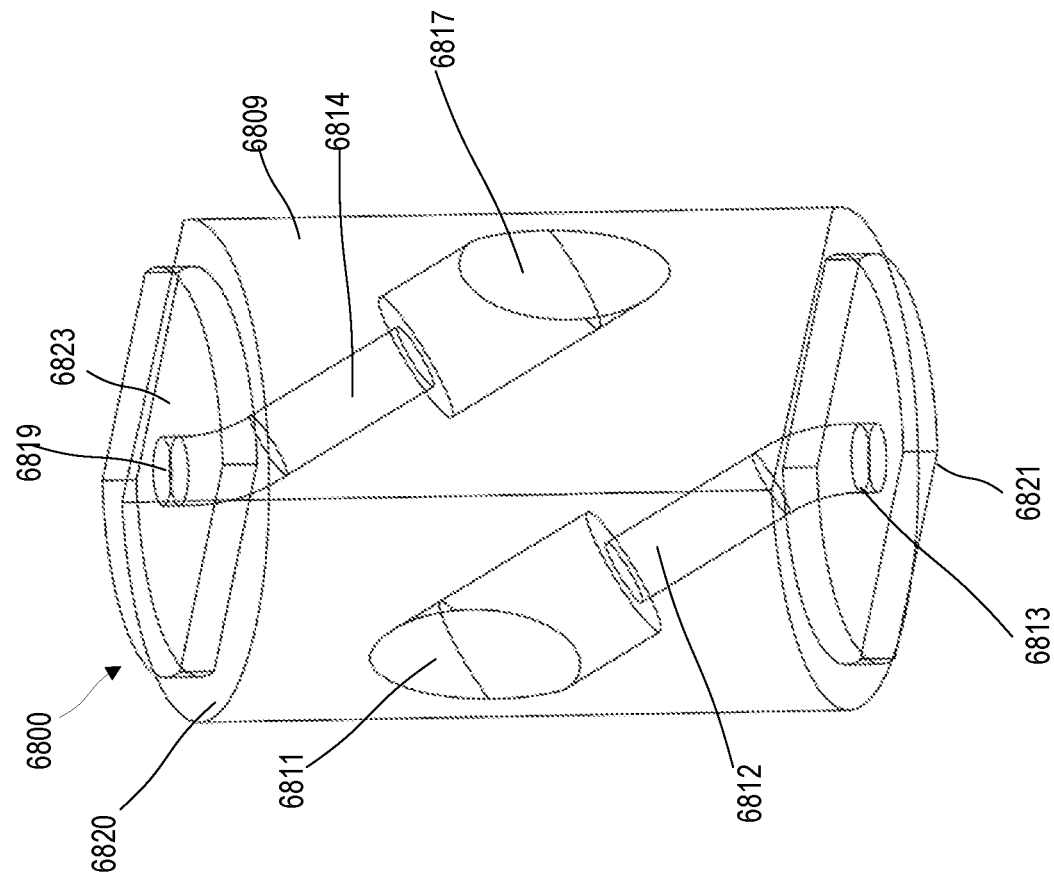
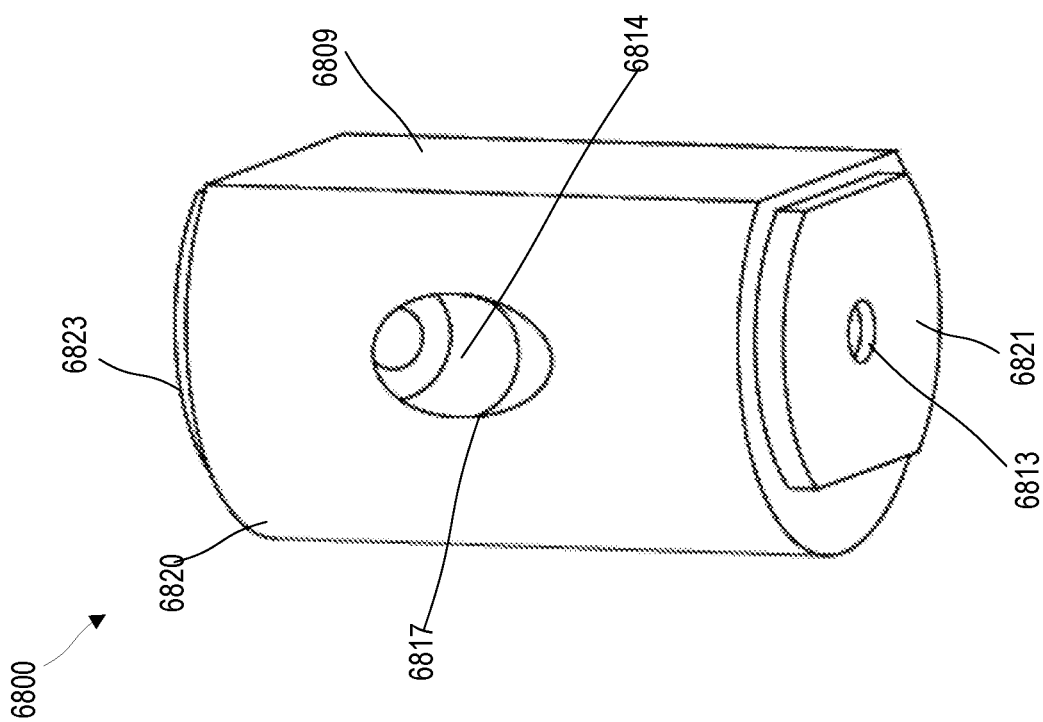
FIG. 17B
FIG. 17A

DEVICES AND METHODS FOR CRIMP INTERFACE FOR CABLE TENSION SENSOR

CROSS-REFERENCE TO RELATED APPLICATIONS

This application claims benefit of priority to U.S. Provisional Application No. 63/213,369 (filed Jun. 22, 2021), entitled "Devices and Methods for Crimp Interface for Cable Tension Sensor," which is incorporated herein by reference in its entirety.

BACKGROUND

The embodiments described herein relate to force sensing mechanical structures, more specifically to medical devices, and still more specifically to instruments used for minimally invasive surgery. More particularly, the embodiments described herein relate to medical devices that include a force sensor unit that is coupled to a mechanical structure of the medical device and is used to measure forces applied to the end effector of the medical device during a surgical procedure.

Known techniques for minimally invasive medical interventions employ instruments to manipulate tissue that can be either manually controlled or controlled via hand-held or mechanically grounded teleoperated medical systems that operate with at least partial computer-assistance ("telesurgical systems"). Many known medical instruments include a therapeutic or diagnostic end effector (e.g., forceps, a cutting tool, or a cauterizing tool) mounted on an optional wrist mechanism at the distal end of a shaft. During a medical procedure, the end effector, wrist mechanism, and the distal end of the shaft are inserted into a small incision or a natural orifice of a patient to position the end effector at a work site within the patient's body. The optional wrist mechanism can be used to change the end effector's position and orientation with reference to the shaft to perform a desired procedure at the work site. In known instruments, motion of the instrument as a whole provides mechanical degrees of freedom (DOFs) for movement of the end effector, and the wrist mechanisms generally provide the desired DOFs for movement of the end effector with reference to the shaft of the instrument. For example, for forceps or other grasping tools, known wrist mechanisms are able to change the pitch and yaw of the end effector with reference to the shaft. A wrist may optionally provide a roll DOF for the end effector, or the roll DOF may be implemented by rolling the shaft. An end effector may optionally have additional mechanical DOFs, such as grip or knife blade motion. In some instances, wrist and end effector mechanical DOFs may be combined. For example, U.S. Pat. No. 5,792,135 (filed May 16, 1997) discloses a mechanism in which wrist and end effector grip DOFs are combined.

To enable the desired movement of the distal wrist mechanism and end effector, known instruments include mechanical connectors (e.g., cables) that extend through the shaft of the instrument and that connect the distal wrist mechanism to a proximal mechanical structure used to move the connectors to operate the wrist mechanism and end effector. For telesurgical systems, the mechanical structure is typically motor driven and operably coupled to a computer processing system to provide a user interface for a clinical user (e.g., a surgeon) to control the instrument as a whole, as well as the instrument's components and functions.

Force sensing surgical instruments are known and together with associated telesurgical systems produce associated haptic feedback to a clinical user during a medical procedure. Such telesurgical system haptic force sensing brings better immersion, realism, and intuitiveness to a clinician performing the procedure. For effective haptics rendering and accuracy, force sensors are placed on a medical instrument within the telesurgical system. One approach is to include a force sensor unit attached to, incorporated within, or both, the proximal mechanical structure of the medical instrument and that can be used to measure forces imparted on or by the end effector of the medical instrument. These force measurements are measured at or near the instrument shaft and are used to produce haptic feedback forces at an input to a master control device to provide to a user an indication of the forces imparted by the medical instrument to, for example, patient tissue. That is, a force imparted by an instrument on objects such as tissue or suture is indicated by a corresponding reactive force from such objects on the instrument, and the sensed reactive force is conveyed to the user as a haptic sensation.

Enhancements to force sensor systems lead to more accurate force measurements, which in turn result in more accurate haptic feedback. For example, including multiple sensors to measure a single force parameter (e.g., the axial reactive force imparted on the end effector) can improve measurement accuracy (e.g., by producing an average measurement or by allowing for subtraction of common modes) and allow for continued instrument operation if one sensor fails. The inclusion of additional sensors, however, competes for the limited space that exists because of the mechanical structure and overall instrument size restrictions required by minimally invasive medical instruments. Force sensor systems must not only be as effective as possible, they must fit within the spatial design constrains of objects experiencing the force, such as medical instruments.

Known force sensing instruments generally sense forces applied to the distal end of the instrument from interaction in the surgical field in three primary directions (e.g., Cartesian Z-axis direction aligned with the instrument shaft longitudinal axis (i.e., axial direction), and X- and Y-directions orthogonal to the axial direction and normal to each other). However, the forces to grip an object without having the object push or pull on the distal end of the instrument in any direction would not be sensed by such force sensing instruments that sense reactive forces in the X-, Y-, or Z-directions. Grip force feedback could be used to convey the force that the surgeon is applying to tissue held between the end effector jaws, for example. Direct measurement of tension of the mechanical connector (e.g., cable) used to to actuate the jaws of an instrument can provide feedback associated with the grip force. But, known mechanisms for coupling a tension sensor to a cable do not always produce a consistent indication of grip force exerted by the jaws.

Thus, a need exists for improved force-sensing capabilities that can provide consistently accurate measurements of tension force on a mechanical connector (e.g., for grip force sensing capabilities), and in turn improve haptic feedback, especially within the spatial constraints of minimally invasive surgical instruments.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter. In some embodiments, a medical device includes an end effector, a mechanical structure, a connector, and a force sensor unit. The mechanical structure includes a drive component, and the connector extends from the drive component to the end effector. Motion of the drive component produces a tension force within the connector, and the tension force is associated with an end effector force exerted by the end effector. The force sensor unit includes a body, a first tube, a second tube, and a strain sensor coupled to the body of the force sensor unit. The body of the force sensor unit includes a first end, a second end opposite from the first end, and a channel extending from the first end through the body to the second end. The first tube is coupled to the first end of the body of the force sensor unit, and the second tube is coupled to the second end of the body of the force sensor unit. The connector includes a first coupling portion, a second coupling portion, and a strain relief portion between the first coupling portion and the second coupling portion. The first coupling portion of the connector is coupled to the force sensor unit within the first tube, the second coupling portion of the connector is coupled to the force sensor unit within the second tube, and the strain relief portion of the connector is in the channel of the body and is free of the tension force.

In some embodiments, the first tube is coupled to the first end of the body of the force sensor unit with a crimp, and the second tube is coupled to the second end of the body of the force sensor unit with a crimp. In some embodiments, the strain sensor is a strain gauge. In some embodiments, the strain sensor is coupled to an electrical wire, and the strain sensor outputs via the electrical wire a signal associated with a strain produced by tension on the connector. In some embodiments the channel of the body is surrounded by the body, and in some embodiments, the channel is C-shaped.

In some embodiments, the force sensor unit further includes an electrical wire coupled to the strain sensor, the connector has a center line along a length of the connector, and the wire is coupled to the body so that the electrical wire extends substantially parallel to the center line of the connector. In such an embodiment, the strain sensor outputs via the electrical wire a signal associated with a strain produced by tension on the connector.

In some embodiments, a medical device includes an end effector, a mechanical structure, a connector, and a force sensor unit. The mechanical structure includes a drive component, and the connector extends from the drive component to the end effector. Rotation of the drive component produces a tension force within the connector, and the tension force is associated with an end effector force exerted by the end effector. The medical device further includes means for coupling the force sensor unit to the connector, means for providing strain relief to a portion of the connector, and means for determining an amount of a force within the strain sensor unit across the portion of the connector to which strain relief is provided.

In some embodiments, the means for determining the amount of the force across the portion of the connector includes the force sensor unit, and the force sensor unit includes a body, a first tube, a second and a strain sensor coupled to the body of the force sensor unit. The body of the force sensor unit includes a first end, a second end opposite from the first end, and a channel extending from the first end through the body to the second end.

In some embodiments, the connector includes a first coupling portion and a second coupling portion, and the means for coupling the force sensor unit to the connector includes a first crimp coupling between the first tube and the first coupling portion of the connector, and a second crimp coupling between the second tube and the second coupling portion of the connector. In some embodiments, the means for providing strain relief to a portion of the connector includes the channel of the body of the force sensor unit. The channel includes an inner diameter that is greater than a diameter of the connector so that the portion of the connector within the channel is free of the tension force. In some embodiments, the channel is surrounded by the body, and in some embodiments, the channel is C-shaped.

In some embodiments, the strain sensor is coupled to an electrical wire, and the strain sensor outputs via the electrical wire a signal associated with a strain produced by the tension force on the connector. In some embodiments, the force sensor unit further includes an electrical wire coupled to the strain sensor, the connector has a center line along a length of the connector, and the wire is coupled to the body so that the electrical wire extends substantially parallel to the center line of the connector. The strain sensor outputs via the electrical wire a signal associated with a strain produced by the tension force on the connector.

In some embodiments, a medical device includes an end effector, a mechanical structure, a connector, and a force sensor unit. The mechanical structure includes a drive component, motion of the drive component produces a tension force within the connector, and the tension force is associated with an end effector force exerted by the end effector. The force sensor unit includes a body and a strain sensor coupled to the body of the force sensor unit, a first channel within the body of the force sensor unit and a second channel within the body of the force sensor unit. The connector includes a first portion and a second portion, and the first portion extends from the drive component to the body and is coupled to the body within the first channel. The second portion of the connector is coupled to the body within the second channel and extends from the body to the end effector.

In some embodiments, the body includes a first opening and a second opening. The first opening is in fluid communication with the first channel, the second opening is in fluid communication with the second channel, an end of first portion of the connector is received through the first opening and coupled to the body within the first opening, and an end of the second portion of the connector is received through the second opening and coupled to the body within the second channel.

In some embodiments, the strain sensor is coupled to an electrical wire and outputs via the electrical wire a signal associated with a strain produced by the tension force within the connector. In some embodiments, the first channel of the body is surrounded by a first portion of the body and the second channel of the body is surrounded by a second portion of the body different than the first portion of the body. In some embodiments, at least one of the first channel or the second channel is C-shaped.

In some embodiments, the force sensor unit further includes an electrical wire coupled to the strain sensor, the connector has a center line along a length of the connector, and the wire is coupled to the body so that the electrical wire extends substantially parallel to the center line of the connector. The strain sensor outputs via the electrical wire a signal associated with a strain produced by the tension force within the connector.

BRIEF DESCRIPTION OF THE DRAWINGS

FIG. 10A is a perspective view of a force sensor unit, according to an embodiment.

FIG. 10B is a cross-sectional view of the force sensor unit of FIG. 10A taken along line 10B-10B in FIG. 10A.

FIG. 10C is a cross-sectional view of the force sensor unit of FIG. 10A taken along line 10B-10B in FIG. 10A and showing a connector extending through the force sensor unit.

FIG. 11A is a perspective view of the force sensor unit of FIG. 10A shown with a cable extending through the force sensor unit.

FIG. 11B is an enlarged side view of the force sensor unit of FIG. 10A.

FIG. 17A is a bottom perspective view of the body of the force sensor unit of FIG. 16A.

FIG. 17B is a perspective view of the body of the force sensor unit of FIG. 16A shown transparent for illustration purposes.

DETAILED DESCRIPTION

Figure 1:
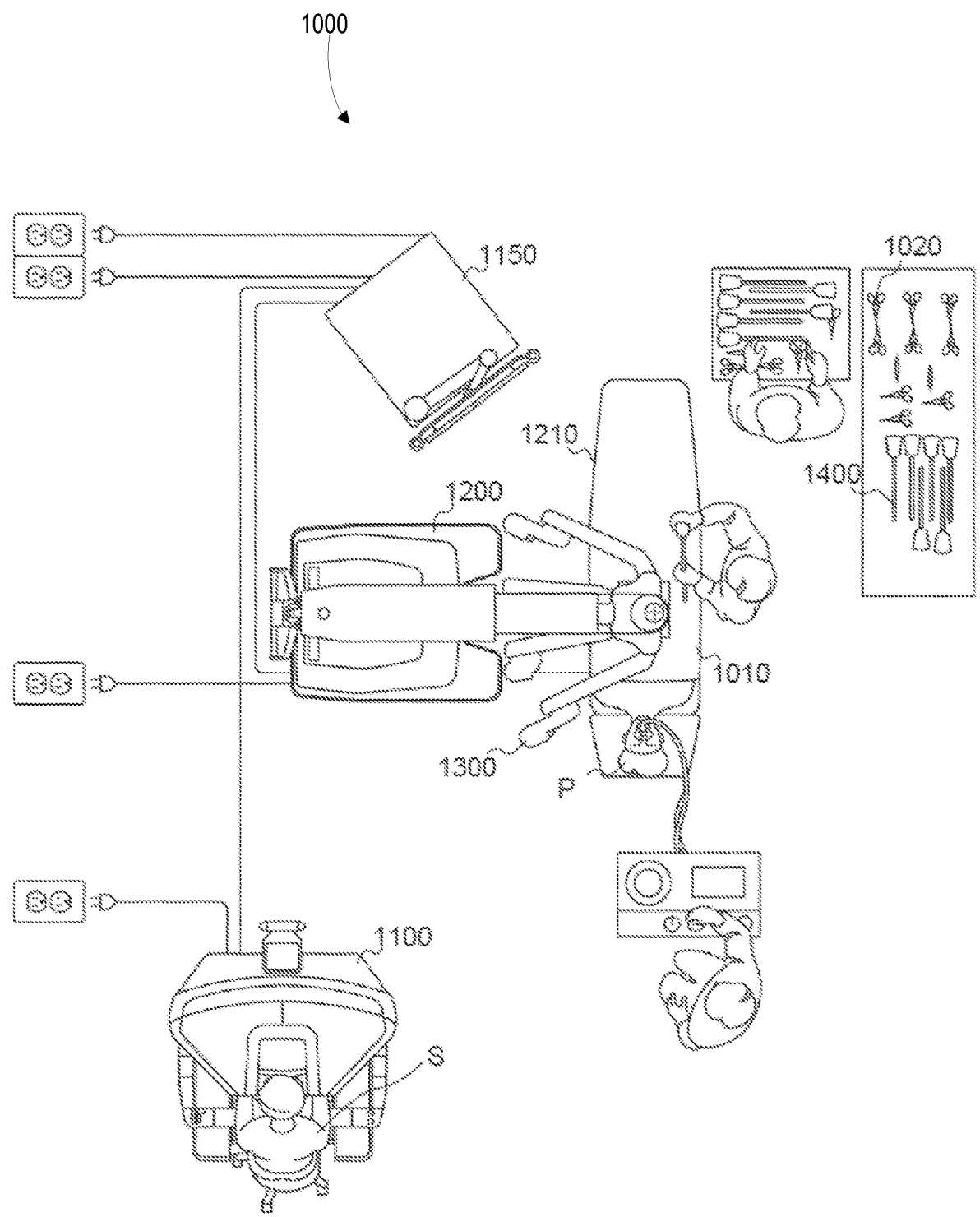
FIG. 1 is a plan view of a minimally invasive teleoperated medical system according to an embodiment being used to perform a medical procedure, such as surgery.

The embodiments described herein can advantageously be used in a wide variety of force sensor applications, such as for grasping, cutting, and manipulating operations associated with minimally invasive surgery. The embodiments described herein can also be used in a variety of non-medical applications such as, for example, teleoperated systems for search and rescue, remotely controlled submersible devices, aerial devices, and automobiles, etc. The medical instruments or devices of the present application enable motion in three or more degrees of freedom (DOFs). For example, in some embodiments, an end effector of the medical instrument can move with reference to the main body of the instrument in three mechanical DOFs, e.g., pitch, yaw, and roll (shaft roll). There may also be one or more mechanical DOFs in the end effector itself, e.g., two jaws, each rotating with reference to a clevis (2 DOFs) and a distal clevis that rotates with reference to a proximal clevis (one DOF). Thus, in some embodiments, the medical instruments or devices of the present application enable end effector motion in all six Cartesian DOFs, with optional additional mechanical or control DOFs for other end effector functions. such as moving one jaw in opposition to another jaw. In other embodiments, instrument end effector motion in one or more Cartesian DOFs may be restricted. The embodiments described herein further can be used to determine the forces exerted on (or by) a distal end portion of the instrument during use.

The medical instruments described herein include a force sensor unit that can be coupled to a connector (e.g., a cable, a band, or the like) of the medical device within a proximal mechanical structure and used to sense force applied at a distal end portion (e.g., an end effector) of the medical device. For example, one or more force sensors, such as strain gauges, can be placed within the cable drive assembly portion of the instrument to measure the force being exerted on one or more cables and the associated torques on the instrument jaws (e.g., at the instrument end effector). The force sensor units described herein are small enough to fit within the instrument's proximal end mechanical structure housing, or optionally within the instrument's shaft between the proximal end mechanical structure and the distal end effector. In addition, the force sensor units describe herein have accurate sensing range over an expected tension range of the instrument cables, have a high stiffness to reduce compliance in the drive assembly, and are easily integrated into the instrument assembly for mass manufacturing. For example, in some embodiments, a force sensor unit is crimped onto a cable to connect a tension sensor in series with a small diameter drive cable. This connection method allows for the sensors to be scaled down to a size that fits within the instrument housing or shaft.

One or more force sensor units described herein are optionally and advantageously incorporated within instruments that have Cartesian X-, Y-, or Z-axis force sensing capabilities for haptic feedback to a user, but do not have the capability to sense instrument grip forces for such haptic feedback. Similarly, one or more force sensor units described herein are optionally and advantageously incorporated within instruments that do not have force sensing capabilities for haptic feedback to a user in order to provide the capability to sense instrument grip forces for such haptic feedback. Likewise, one or more force sensor units described herein are optionally and advantageously incorporated within instruments for haptic force sensing capabilities other than instrument grip forces for such haptic feedback. And further, one or more force sensor units described herein are optionally and advantageously incorporated within instruments for purposes other than force sensing capabilities for haptic feedback to an operator, such as to allow for cable tension to be more accurately controlled and monitored during teleoperation.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

As used in this specification and the appended claims, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to the actuation shaft) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® surgical system, commercialized by Intuitive Surgical, Inc. of Sunnyvale, California. Examples of such surgical systems are the da Vinci Xi® surgical system (Model IS4000), and the da Vinci X® surgical system (Model IS4200). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® surgical systems (e.g., the Model IS4000, the Model IS3000, the Model IS2000, the Model IS1200, the Model SP1099) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

FIG. 1 is a plan view illustration of a computer-assisted teleoperation system. Shown is a medical device, which is a Minimally Invasive Robotic Surgical (MIRS) system 1000 (also referred to herein as a minimally invasive teleoperated surgery system that operates with at least partial computer support—a telesurgical system), used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot) and an optional auxiliary equipment unit 1150. The manipulator unit 1200 can include an arm assembly 1300 and a tool assembly removably coupled to the arm assembly. The manipulator unit 1200 can manipulate at least one removably coupled instrument 1400 through a minimally invasive incision in the body or natural orifice of the patient P while the surgeon S views the surgical site and controls movement of the instrument 1400 through control unit 1100. An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of instruments 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 2:
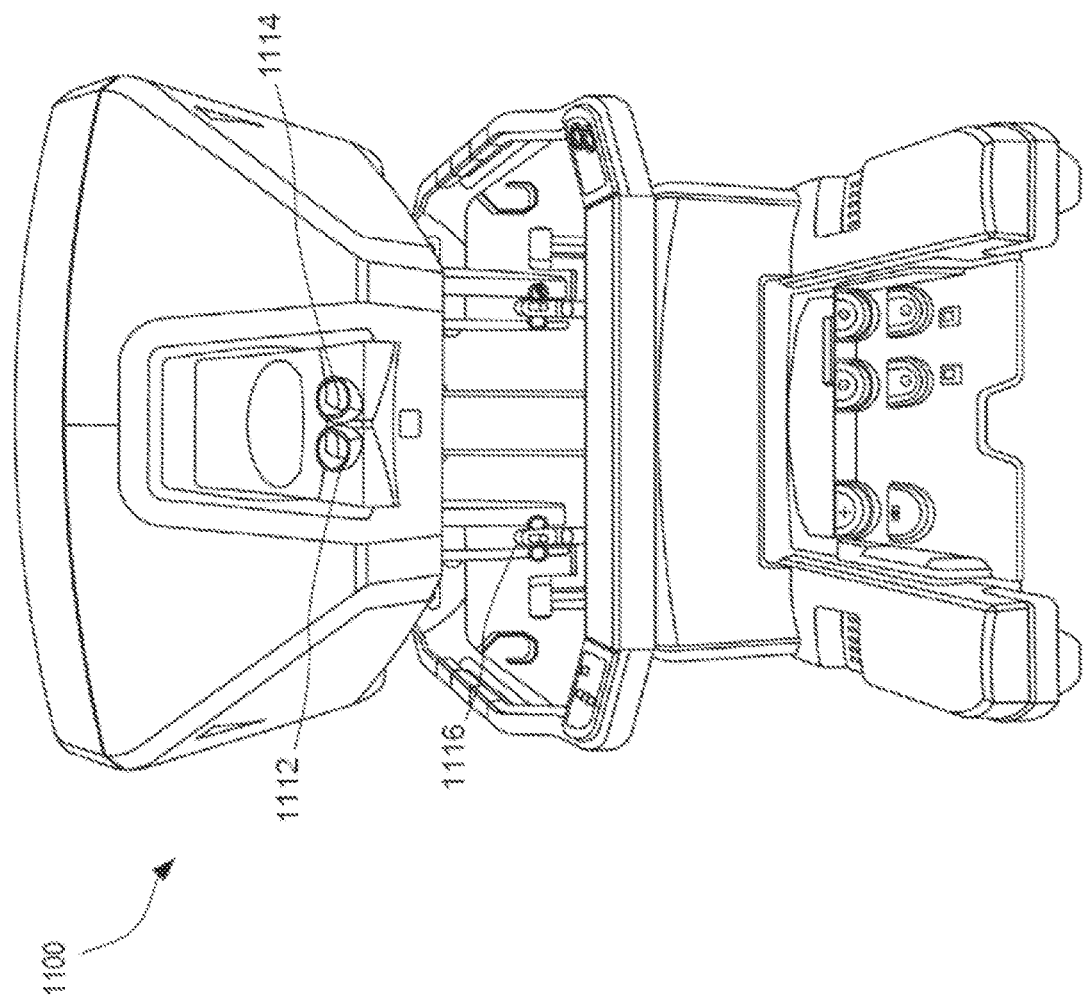
FIG. 2 is a perspective view of an optional auxiliary unit of the minimally invasive teleoperated surgery system shown in FIG. 1.

FIG. 2 is a perspective view of the control unit 1100. The user control unit 1100 includes a left eye display 1112 and a right eye display 1114 for presenting the surgeon S with a coordinated stereo view of the surgical site that enables depth perception. The user control unit 1100 further includes one or more input control devices 1116, which in turn cause the manipulator unit 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, strain, or tactile feedback sensors (not shown), or any combination of such sensors, may be employed to transmit position, force, or tactile sensations, or any combination of such sensations, from the instruments 1400 back to the surgeon's hand or hands through the one or more input control devices 1116.

The user control unit 1100 is shown in FIG. 1 as being in the same room as the patient so that the surgeon S can directly monitor the procedure, be physically present if necessary, and speak to an assistant directly rather than over the telephone or other communication medium. In other embodiments, however, the user control unit 1100 and the surgeon S can be in a different room, a completely different building, or other remote location from the patient allowing for remote surgical procedures.

Figure 3:
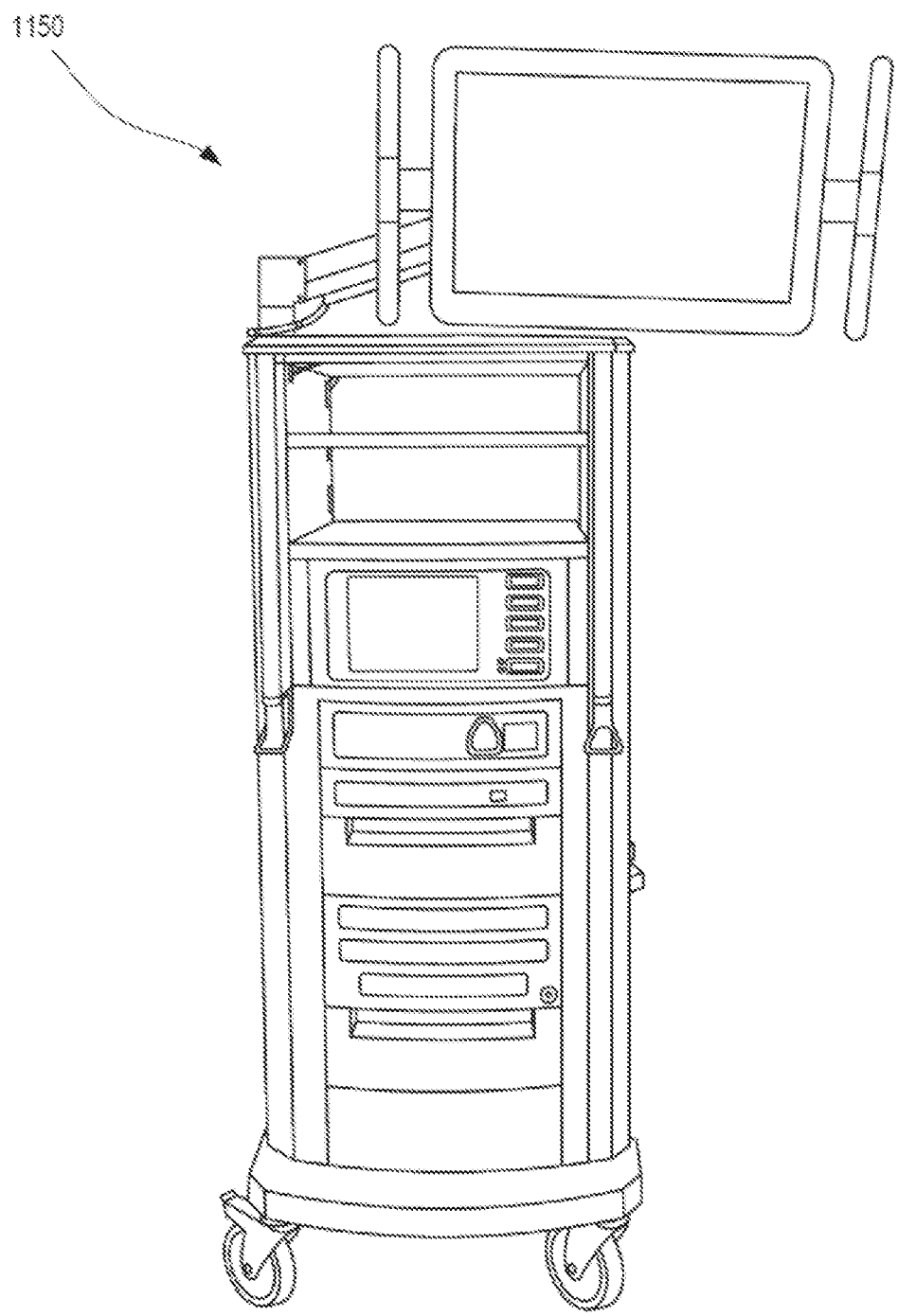
FIG. 3 is a perspective view of a user control console of the minimally invasive teleoperated surgery system shown in FIG. 1.

FIG. 3 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
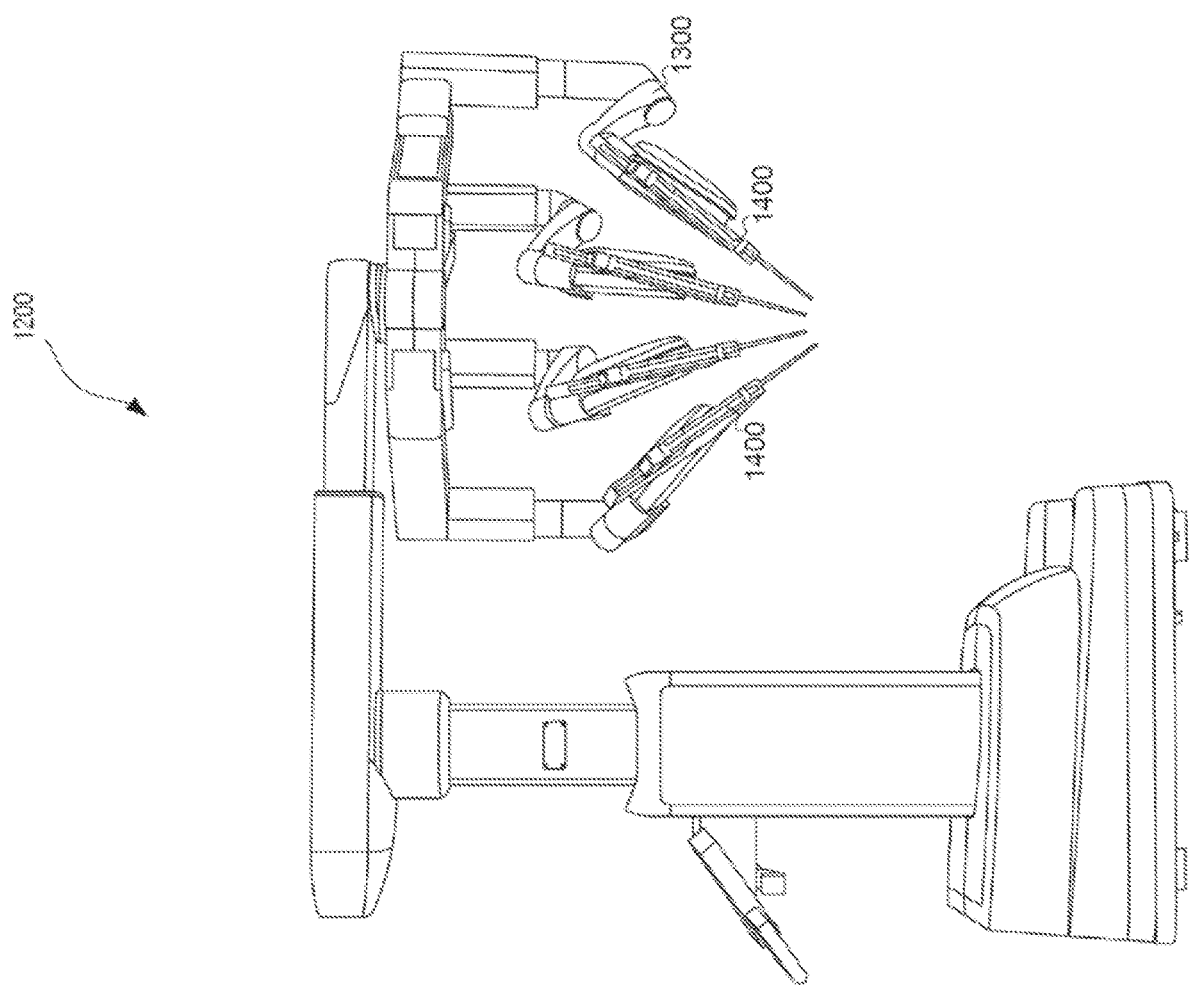
FIG. 4 is a front view of a manipulator unit, including a plurality of instruments, of the minimally invasive teleoperated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having a number of joints. Moreover, the instruments 1400 and the imaging device are positioned and manipulated through incisions or natural orifices in the patient P in a manner such that a center of motion remote from the manipulator and typically located at a position along the instrument shaft is maintained at the incision or orifice by either kinematic mechanical or software constraints. In this manner, the incision size can be minimized.

Figure 5:
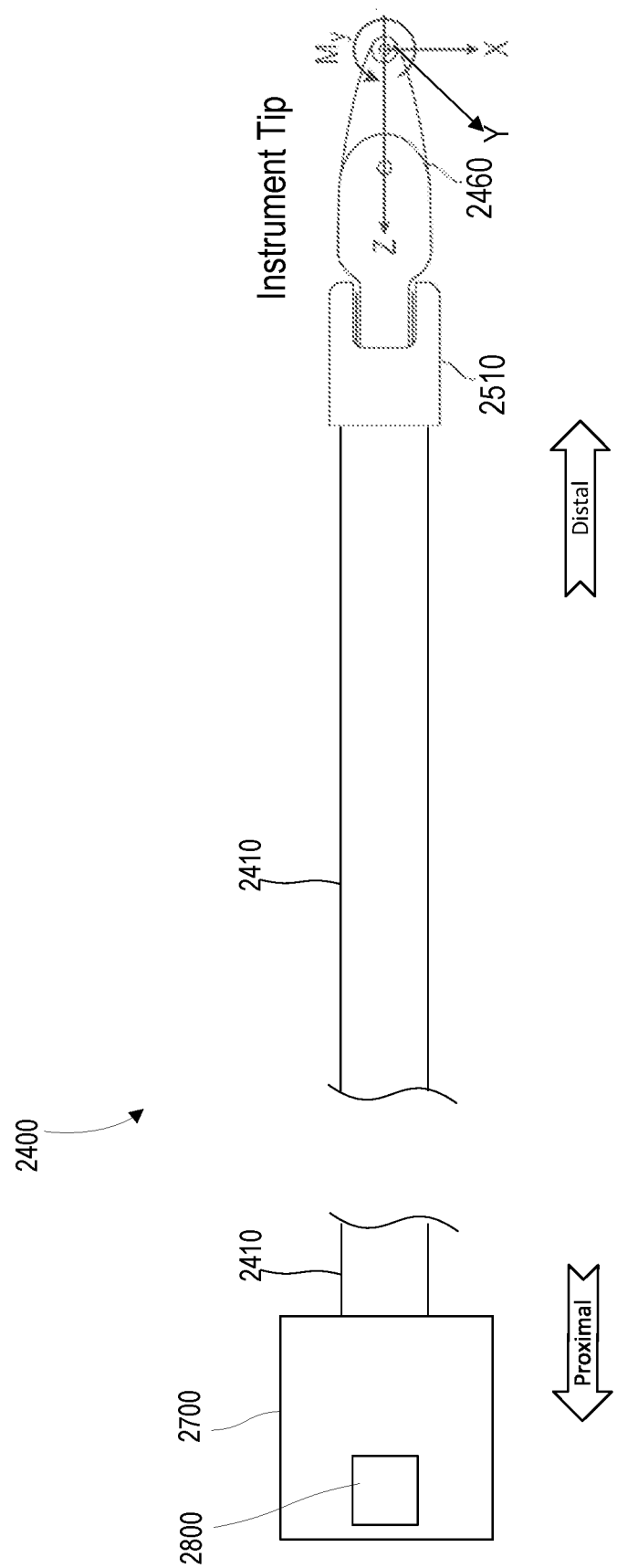
FIG. 5 is a diagrammatic illustration of a medical device including a force sensor unit, according to an embodiment.

FIG. 5 is a schematic illustration of a medical device 2400, according to an embodiment. In some embodiments, the medical device 2400 or any of the components therein are optionally parts of a surgical system that performs surgical procedures, and which can include a manipulator unit, a series of kinematic linkages, a series of cannulas, or the like. The medical device 2400 (and any of the instruments described herein) can be used in any suitable surgical system, such as the MIRS system 1000 illustrated and described above. In this embodiment, the medical device 2400 includes a proximal mechanical structure 2700, a shaft 2410 coupled to the mechanical structure 2700, and an end effector 2460 coupled at a distal end portion of the shaft 2410. The end effector 2460 can include, for example, articulatable jaws or another suitable surgical tool that is coupled to a link 2510. In some embodiments, the link 2510 can be included within a wrist assembly having multiple articulating links. In some embodiments, the distal end portion of the shaft 2410 is coupled to the end effector 2460 via another coupling component (such as an anchor or coupler, not shown). The shaft 2410 is also movably coupled at a proximal end portion to the mechanical structure 2700. The mechanical structure 2700 can include components configured to move one or more components of the surgical instrument, such as, for example, the end effector 2460. The mechanical structure 2700 can be similar to the mechanical structure 5700 described in more detail below with reference to medical device 5400.

Generally, during a medical procedure, the end effector 2460 contacts anatomical tissue, which may result in Cartesian X-, Y-, or Z-axis direction forces being imparted on the end effector 2460 and that may result in moment forces such as a moment $M_Y$ about a Y-direction axis as shown in FIG. 5. In some embodiments, one or more strain sensors (not shown), which can be electrically resistive strain gauges, can be coupled to the beam 2810 to measure strain in the beam 2810. The measured beam strain can be used to determine forces imparted on the end effector 2460 in the X- and Y-axis directions. These X- and Y-axis forces are transverse (e.g., perpendicular) to the Z axis (which is defined to be parallel to or collinear with a center axis of the beam $A_B$).

In some embodiments, the medical device 2400 can also be capable of measuring the axial force(s) (i.e., in the direction of the Z-axis) imparted on the end effector 2460. For example, an axial force $F_Z$ imparted to the end effector 2460 in a direction of the Z-axis can cause axial displacement of the shaft 2410 in a direction along a center axis of the shaft 2410. The axial force $F_Z$ may be in the proximal direction (e.g., a reactive force resulting from pushing against tissue with the end effector), or it may be in the distal direction (e.g., a reactive force resulting from pulling tissue grasped with the end effector). In some embodiments, the shaft 2410 can be coupled to the mechanical structure 2700 via a biasing mechanism (e.g., a linkage or a spring-loaded coupling, not shown) such that the amount of travel of the shaft 2410 relative to the mechanical structure 2700 can be correlated to the magnitude of the axial force $F_Z$ imparted to the end effector 2460. In this manner, measuring the distance through which the shaft 2410 moves relative to the mechanical structure 2700 can be used to determine the axial force $F_Z$.

Figure 6B:
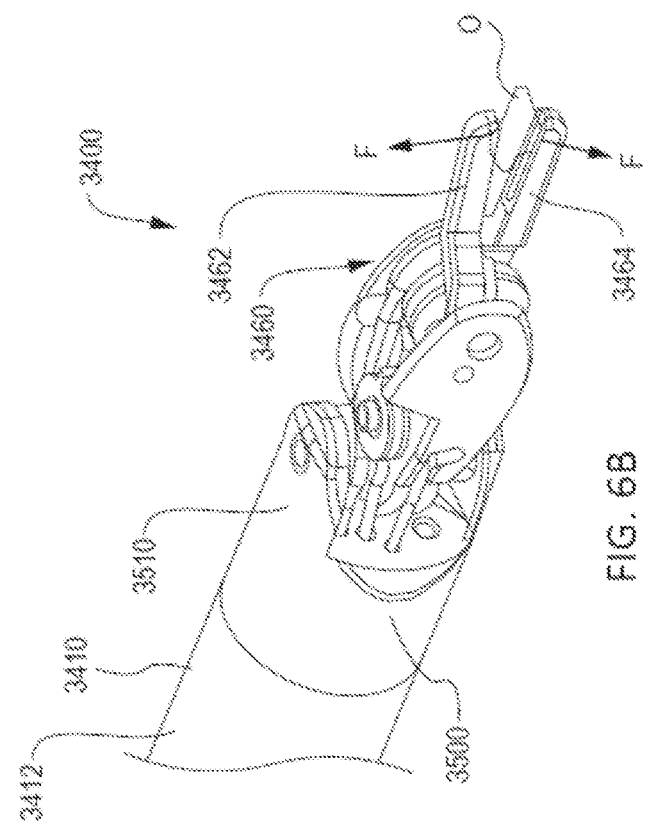
FIG. 6B is an illustration of the distal end portion of the medical device of FIG. 6A shown in a second configuration grasping an object.
Figure 6A:
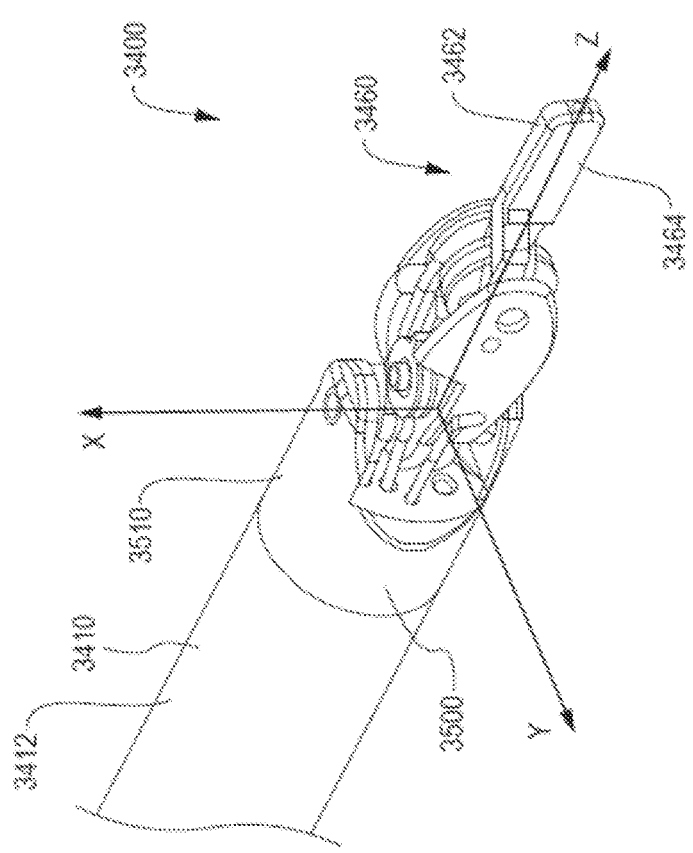
FIG. 6A is an illustration of a distal end portion of a medical device shown in a first configuration, according to an embodiment.

FIGS. 6A and 6B are illustrations of a distal end portion of an embodiment of a medical device 3400 illustrating grip forces at a distal tip of the medical device. The medical device 3400 includes a shaft 3410 having a proximal end portion (not shown) coupled to a mechanical structure (not shown), and a distal end portion 3412 coupled to an end effector 3460 via a link 3510 of a wrist assembly 3500. As described above, the end effector 3460 can include, for example, articulatable jaws 3462, 3464 or another suitable surgical tool, and the end effector 3460 can be coupled to the wrist assembly 3500. In some embodiments, a force sensor unit (not shown) can optionally be included in the instrument 3400 (and any of the instruments described herein) to detect forces applied on the instrument tip in three orthogonal directions: Z, oriented along the shaft axis, and X and Y, oriented perpendicular to the shaft axis and normal to each other as shown in FIG. 6A. X and Y forces can be sensed through strain gauges on the instrument shaft, and Z forces can be sensed through the displacement of the shaft.

When an object O (e.g., tissue, suture, a suture needle) is gripped between the jaws 3462, 3464 of the end effector 3460, a reactive force F is imparted on the jaws 3462, 3464 as the jaws grip the object, as shown in FIG. 6B. This reactive force on the jaws represents the grip force the jaws are imparting on the object. With such a grip force, however, there is no resultant component straining the instrument tip in the X, Y, and Z directions. Thus, any force sensing capabilities for sensing forces in the X, Y, or Z axes would not sense the grip force because there would be no force to deflect the tip in the three primary directions (X, Y and Z). And so, the instrument 3400 (and the other embodiments described herein) provides feedback to the user of the force being used to grip the object by measuring tension of one or more cables that actuate the jaws 3462, 3464.

Figure 7:
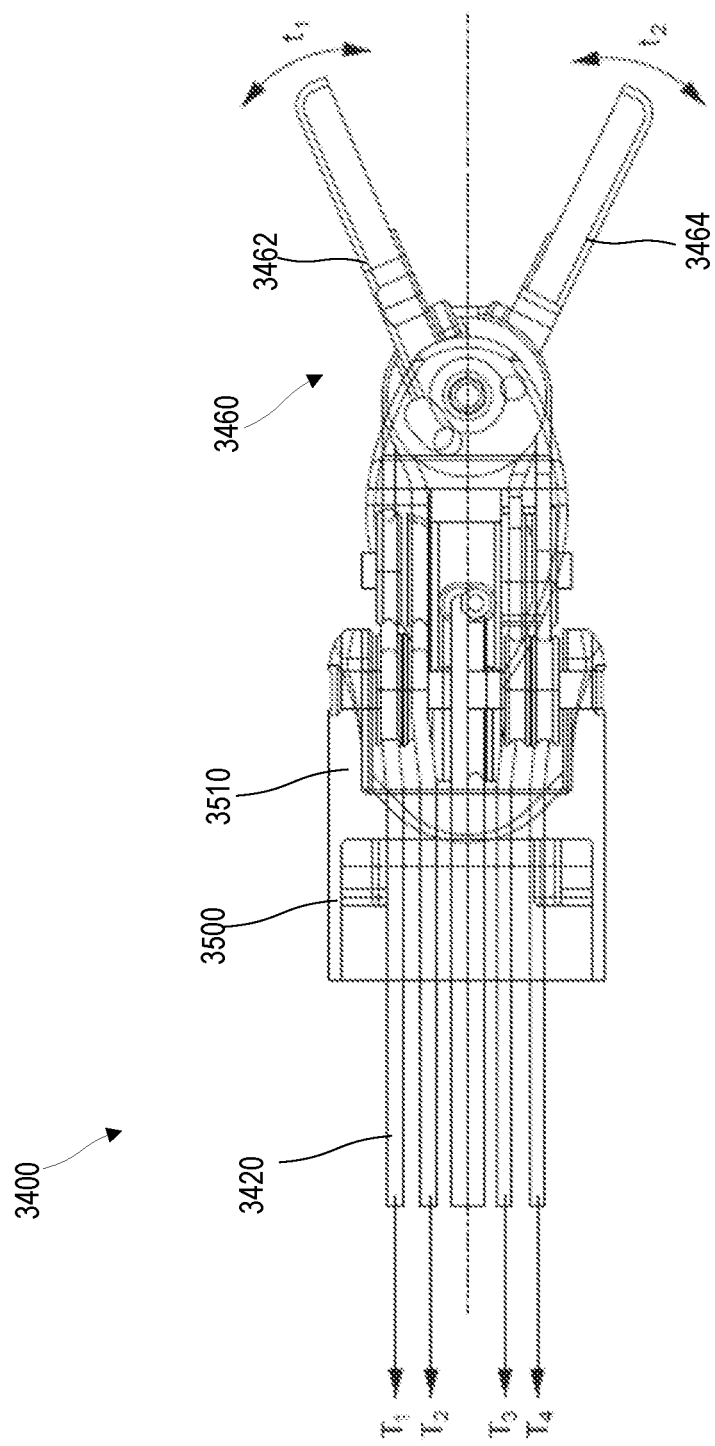
FIG. 7 is a top view of the distal end portion of the medical device of FIG. 6A.

More specifically, FIG. 7 illustrates torques $t_1$ and $t_2$ at the distal grip portion (end effector 3460) of the medical instrument 3400. The torques $t_1$ and $t_2$ resulting from grasping of tissue induces tensions $T_1$-$T_4$ within the drive cables 3420. In some situations one or more of the tensions $T_1$-$T_4$ may drop to zero, and in other situations the manipulator unit controls the tensions $T_1$-$T_4$ to remain above zero. With knowledge of the grip pulley diameters, tensions measured in one or more of the drive cables 3420 can be correlated to the torques at the instrument grips. Without a tension sensor, torque at the instrument grip can be estimated based on the current being drawn by a motor driving the cable tension, such as a motor within the telesurgical system's instrument carriage. But correlation between the motor current and torque at the instrument grip is complicated by friction within the gearbox and losses within the instrument cable drive train. Therefore, direct sensing of the instrument cable tensions improves measurement certainty of the actual grip torques at the instrument end effector 3460.

Figure 8A:
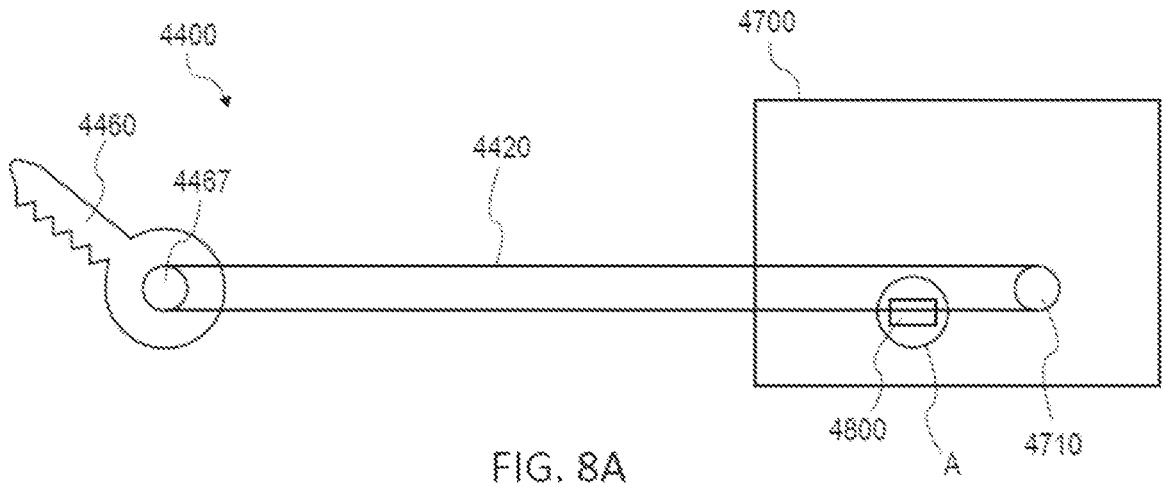
FIGS. 8A-8C are each a schematic illustration of a medical device according to different embodiment.
Figure 8B:
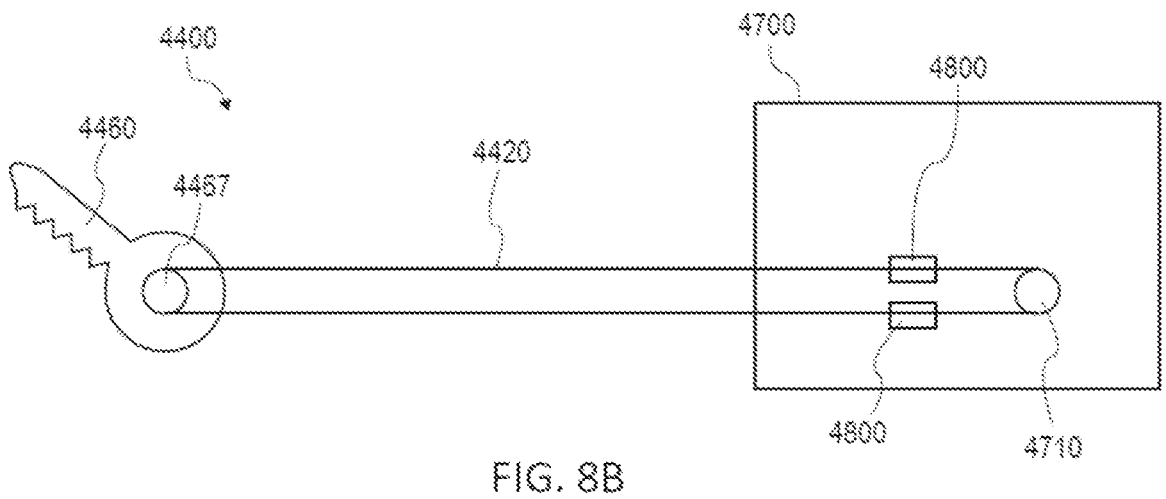
Figure 8C:
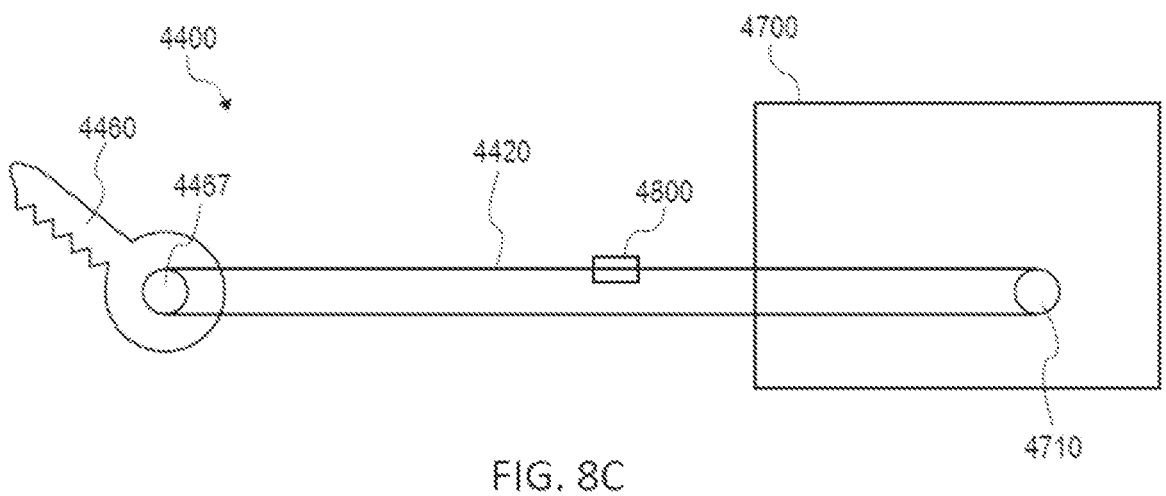
Figure 9:
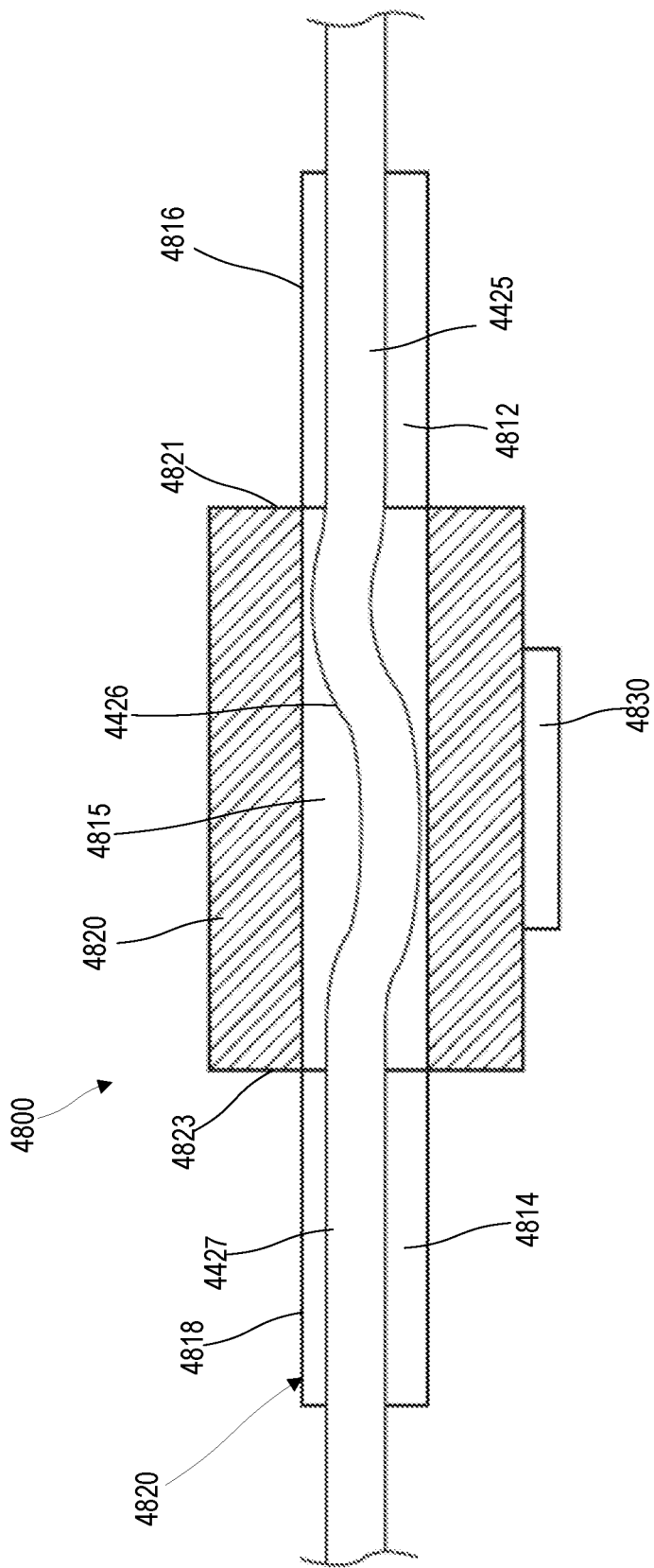
FIG. 9 is an enlarged diagrammatic cross-sectional view of encircled portion A of the medical device shown in FIG. 8A.
Figure 12:
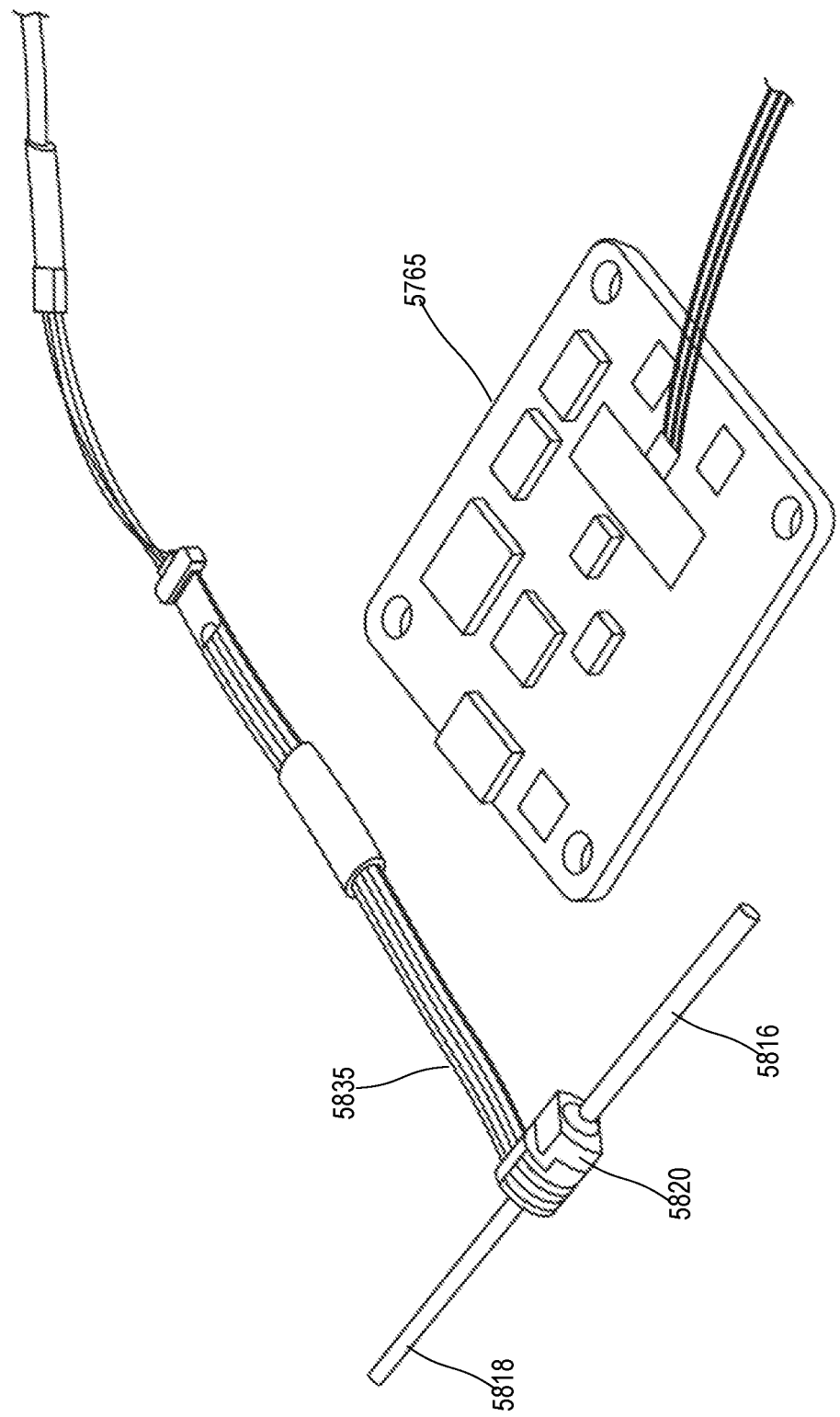
FIG. 12 is a perspective view of the force sensor unit and circuit board of the medical device of FIG. 13.

FIG. 8A is a schematic illustration of a medical device 4400 according to an embodiment, and FIG. 9 is an enlarged view of the encircled portion A in FIG. 8A. In some embodiments, the medical device 4400 or any of the components therein are optionally parts of a surgical system that performs surgical procedures, and which can include a manipulator unit, a series of kinematic linkages, a series of cannulas, or the like. The medical device 4400 (and any of the instruments described herein) can be used in any suitable surgical system, such as the MIRS system 1000 shown and described above. As shown in FIG. 8A, the medical device 4400 includes a mechanical structure 4700, a drive component 4710 (e.g., capstan) within the mechanical structure 4700, an end effector 4460 coupled to or including a drive pulley 4467, and a connector 4420 (e.g., cable) coupled between the drive pulley 4467 and the drive component 4710. The end effector 4460 can be actuated to move by the drive component 4710 via the connector 4420. In this embodiment, a force sensor unit 4800 is coupled to the connector 4420 within the mechanical structure 4700. In some embodiments, as shown in FIG. 8B, more than one force sensor unit 4800 can be coupled to a connector 4420 within the mechanical structure 4700. For example, in some embodiments a force sensor unit 4800 can be coupled to each end of a cable pair. In some embodiments, a force sensor unit 4800 can be coupled to a connector 4420 outside of the proximal mechanical structure 4700, either in addition to a force sensor unit within the mechanical structure or alternatively as a substitute for a force sensor unit within the mechanical structure. For example, a force sensor unit 4800 can be coupled to a connector 4420 at a location between the mechanical structure 4700 and the end effector 4460 as shown in FIG. 8C.

In some embodiments, the connector 4420 can optionally be a cable, a band, or the like sufficient to convey tension from the drive component to the driven component. And in some embodiments, connector 4420 includes a first cable portion within mechanical structure 4700 that is coupled to force sensor unit 4800, and a second cable portion in contact with the driven component 4467. In some embodiments, another component such as a hypotube can be coupled between the first and second cable portions to provide improved tension force transmission.

As described above, the end effector 4460 can include, for example, one or more articulatable jaws or another suitable surgical tool and can be coupled to a link (not shown). In some embodiments, the link can be included within a wrist assembly having multiple articulating links. In some embodiments the drive pulley 4467 is part of the link or the wrist assembly. The medical device 4400 can also include a shaft (not shown) coupled at a proximal end portion to the mechanical structure 4700 and through which or along which the connector 4420 can extend. The drive component 4710 of the mechanical structure 4700 can be configured to move one or more components of the surgical instrument, such as, for example, the end effector 4460 (e.g., via the connector 4420 and drive pulley 4467). The mechanical structure 4700 can be similar to the mechanical structure 5700 described in more detail below with reference to medical device 5400.

As shown in FIG. 9, the force sensor unit 4800 includes a body 4820, and an internal channel 4815 is defined within the body and extends through the body from a first end 4821 of the body to a second end 4823 of the body as shown. A first tube 4816 is coupled to the first end 4821 of the body 4820, and a second tube 4818 is coupled to the second end 4823 of the body 4820. The first tube 4816 and the second tube 4818 can be coupled to the body 4420 with various different coupling methods. For example, in some embodiments, the first tube 4816 and the second tube 4818 can be welded to the body 4820. A sensor 4830 is coupled to an exterior of the body 4820. In some embodiments, the sensor 4830 can be any type of force or pressure element such as a strain gauge (e.g., an electrically resistive strain gauge) or a piezoelectric or piezoresistive force sensing element (e.g., strain gauge or MEMS, etc.).

A channel 4812 is defined within the first tube 4816 and extends axially within the first tube 4816 between a first end and a second end of the first tube 4816. Similarly, a channel 4814 is defined within the second tube 4818 and extends axially through the second tube 4818. Each tube channel is in fluid communication with the channel 4815 of the body 4820 so that a single channel extends through the assembly of the body and the tubes. As shown in FIG. 9, the connector 4420 extends through the channel 4812 of the first tube 4816, the channel 4815 of the body 4820, and the channel 4814 of the second tube 4818. More specifically, the connector 4420 includes a first coupling portion 4425 within the channel 4812 of the first tube 4816, a second coupling portion 4427 within the channel 4814 of the second tube 4818, and a strain relief portion 4426 between the first coupling portion 4425 and the second coupling portion 4427 within the channel 4815 of the body 4820. The first connector portion 4425 is fixedly coupled to the first tube 4816, and the second connector portion 4427 is fixedly coupled to the second tube 4818. Since the connector portion 4425 is fixedly coupled to the first tube, it is fixedly coupled to the first end 4821 of the sensor body 4820. Similarly, since the connector portion 4427 is fixedly coupled to the second tube, it is fixedly coupled to the second end 4823 of the sensor body 4820. Thus sensor body 4820 is fixedly coupled between connector portions 4425, 4427 of the connector 4420 (i.e., the sensor body is coupled in-line with the connector). The first coupling portion 4425 can be coupled within the first tube 4816 and the second coupling portion 4427 can be coupled within the second tube 4818 by any suitable means. For example, in some embodiments, the coupling portions can be coupled within the tubes via a crimp connection. In other embodiments, the coupling portions can be coupled within the tubes via an adhesive. In yet other embodiments, the coupling portions can be coupled within the tubes via a weld.

The strain relief portion 4426 of the connector 4420 remains free within the channel 4815 of the body 4820 (e.g., not crimped or fixedly secured to the body 4820). Further, the strain relief portion 4426 is positioned within the channel 4815 with slack to provide a tension-free portion of the connector 4420. When assembled within the medical device 4400, the connector 4420 is in tension and extends through the channels (4412, 4414 and 4415) of the force sensor unit 4800, parallel to a longitudinal axis of the body 4820. During use of the medical device 4400, drive component 4710 produces tension in the connector 4420, which in turn produces torque at the drive pulley 4467, that causes the jaws of the end effector 4460 to open and close. When the jaws are closed onto an object, such as a portion of tissue, a force is exerted onto the object that are being gripped by the jaws. This grip force is associated with the tension in the connectors 4420 and vice-versa.

With the first tube 4816 and second tube 4818 coupled to (e.g., crimped or welded onto) the connector 4420, and with strain relief portion 4426 not under tension, the first tube 4816, the second tube 4818, and the sensor body 4820 bear the entire tension force imparted to the connector 4420, which can be measured by the sensor 4830 on the body 4820 of the force sensor unit 4800. But if a portion of the connector 4420 within the channel 4815 is under tension, the full tensile force imparted on the connector 4420 would not be received by the sensor 4830. Thus, providing a slack portion (i.e., strain relief portion 4426) of the connector 4420, having no tension imparted to it, allows for the full tensile force imparted on the connector 4420 to be accurately read through the connection of the first tube 4816 and the second tube 4818 to the first coupling portion 4425 and the second coupling portion 4427 of the connector 4420, respectively. Without the slack portion, the tensile force read by the sensor 4830 would not accurately capture the full tensile force imparted on the connector 4420.

In some embodiments, rather than providing a slack portion of the connector 4420 as described above, the connector 4420 can include two separate portions, with one portion coupled to the first tube 4816 and the other portion coupled to the second tube 4818. Thus a break in the connector 4420 is created and the full tensile force imparted on the connector 4420 can be accurately read through the connection of the first portion of the connector 4420 that is connected to the first tube 4816 and the second portion of the connector 4420 that is connected to the second tube 4818.

In some embodiments, the channel 4815 of the body 4820 completely surrounds the connector 4420. In some embodiments, the channel 4815 may have, for example, a C-shaped cross-section such that the channel 4815 has a portion that is open. In some such embodiments, the first tube 4816 and the second tube 4818 can also have a C-shaped cross-section such that the connector 4420 can be placed within the channel 4815, the channel 4812, and the channel 4814 through the C-shaped openings after the instrument 4400 has been assembled. Said another way, the C-shaped opening eliminates the need to thread the force sensor unit 4800 over the connector 4420. The first tube 4816 and the second tube 4818 can then be crimped or otherwise secured to the connector 4420.

The sensor 4830 can be coupled to an electrical wire (not shown in FIGS. 8A-8C and 9) such that the sensor outputs a signal associated with a strain produced by tension on the connector 4420 via the electrical wire. In some embodiments, the connector 4420 has a centerline along a length of the connector 4420, and the electrical wire is coupled to the body 4820 so that the electrical wire extends substantially parallel to the centerline of the connector 4420. In some embodiments, the electrical wire is coupled to the body 4820 so that the electrical wire extends transverse (e.g., perpendicular) to the centerline of the connector 4420.

During use of the medical device 4400, motion of the drive component 4720 produces a tension force within the connector 4420, and that tension force is associated with an end effector force exerted by the end effector 4460. As described above, as the end effector 4460 grips an object, a force is imparted at the jaws of the end effector 4460, and that force results in the tension force within the connector 4420. The sensor 4830 of the force sensor unit 4820 can be used to measure the strain (e.g., tension force) on the connector 4420, which in turn can be correlated to the force imparted on the end effector 4460. As described above with reference to FIG. 7, with knowledge of the drive pulley diameter, tensions measured in the connector 4420 can be correlated to the torques at the end effector jaws (e.g., grips).

FIGS. 10A-12 illustrate an embodiment of a fore sensor unit 5800 that can be used within a medical device, such as medical device 5400 shown and described with reference to FIGS. 13A-15. The force sensor unit 5800 includes a body 5820, and an internal channel 5815 is defined within the body 5820 and extends through the body 5820 from a first end 5821 of the body to a second end 5823 of the body as shown. A first tube 5816 is coupled to the first end 5821 of the body 5820 and a second tube 5818 is coupled to the second end 5823 of the body 5820. A sensor 5830 (shown in FIGS. 11B) is coupled to an exterior surface 5809 of the body 5820.

A channel 5812 is defined within the first tube 5816 and extends axially within the first tube 5816 between a first end and a second end of the first tube 5816. Similarly, a channel 5814 is defined within the second tube 5818 and extends axially through the second tube 5818. The channel 5812, and the channel 5814 are each in communication with the channel 5815 of the body 5820. As described above for previous embodiments, a connector 5420 (see, e.g., FIGS. 10C, 11A and 12) extends through the channel 5812 of the first tube 5816, the channel 5815 of the body 5820, and the channel 5814 of the second tube 5818. The connector 5420 can be, for example, a cable, a band, or the like. More specifically, as shown in FIG. 10C, the connector 5420 includes a first coupling portion 5425 within the channel 5812 of the first tube 5816, a second coupling portion 5427 within the channel 5814 of the second tube 5818, and a strain relief portion 5426 between the first coupling portion 5425 and the second coupling portion 5427 disposed within the channel 5815 of the body 5820.

As described above for the previous embodiment, the strain relief portion 5426 of the connector 5420 remains free within the channel 5815 of the body 5820 (e.g., not crimped or fixedly secured to the body 5820). Further, the strain relief portion 5426 is positioned within the channel 5815 with slack to provide a tension-free portion of the connector

5420. When assembled within the medical device 5400, the connector 5420 is in tension and extends through the channels (5812, 5814 and 5815) of the force sensor unit 5800, parallel to a longitudinal axis of the body 4820. During use of the medical device 5400, drive component 5710 (described below) produces tension in the connector 5420, which in turn produces torque at the drive pulley of the end effector 5460, (described below), that causes the jaws of the end effector 5460 to open and close. When the jaws are closed onto an object, such as a portion of tissue, a force is exerted onto the object that is being gripped by the jaws. This grip force is associated with the tension in the connector 5420 and vice-versa.

With the first tube 5416 and second tube 5418 fixedly coupled onto the connector 5420, the first tube 5816 and the second tube 5818 can bear the entire tension force imparted to the connector 5420, which can be measured by the sensor 5830 on the body 5820 of the force sensor unit 5800. If, however, a portion of the connector 5420 within the channel 5815 is under tension, the full tensile force imparted on the connector 5420 would not be received by the sensor 5830 (e.g., the entire tension would not be transmitted via the body 5820 for detection by the sensor). Thus, providing a slack portion (i.e., strain relief portion 5426) of the connector 5420, having no tension imparted to it, allows for the full tensile force imparted on the connector 5420 to be accurately read through the connection of the first tube 5816 and the second tube 5818 to the first coupling portion 5425 and the second coupling portion 5427 of the connector 5420, respectively. Without the slack portion, the tensile force read by the sensor 5830 would not accurately capture the full tensile force imparted on the connector 5420. As described above, in other embodiments, a slack portion may not be provided and instead the connector 5420 has two portions, one fixedly coupled to the first tube 5816 and the other fixedly coupled to the second tube 5818.

As described herein, the sensor 5830 can be, for example, any type of force or pressure element such as a strain gauge (e.g., an electrically resistive strain gauge) or a piezoelectric or piezoresistive force sensing element (e.g., strain gauge or MEMS, etc.). The sensor 5830 can be coupled to an electrical wire 5835 (see FIG. 12) which is coupled to a circuit board 5765 (see FIG. 12) such that the sensor 5830 can output a signal via the electrical wire 5835 that is associated with a strain produced by tension on the connector 5420. In this embodiment, the electrical wire 5835 is coupled to the sensor 5830 such that the electrical wire 5835 extends transverse (e.g., perpendicular) to a centerline along a length of the body 5820 and a centerline along a length of the connector 5420. In other embodiments, the electrical wire 5835 can be coupled to the sensor 5830 such that the electrical wire 5835 extends substantially parallel to the centerline of the connector 5420 and the centerline of the body 5820. In some embodiments, having the electrical wire 5835 extend parallel to the connector 5420 can improve the routing and packaging within the mechanical structure 5400.

Figure 13:
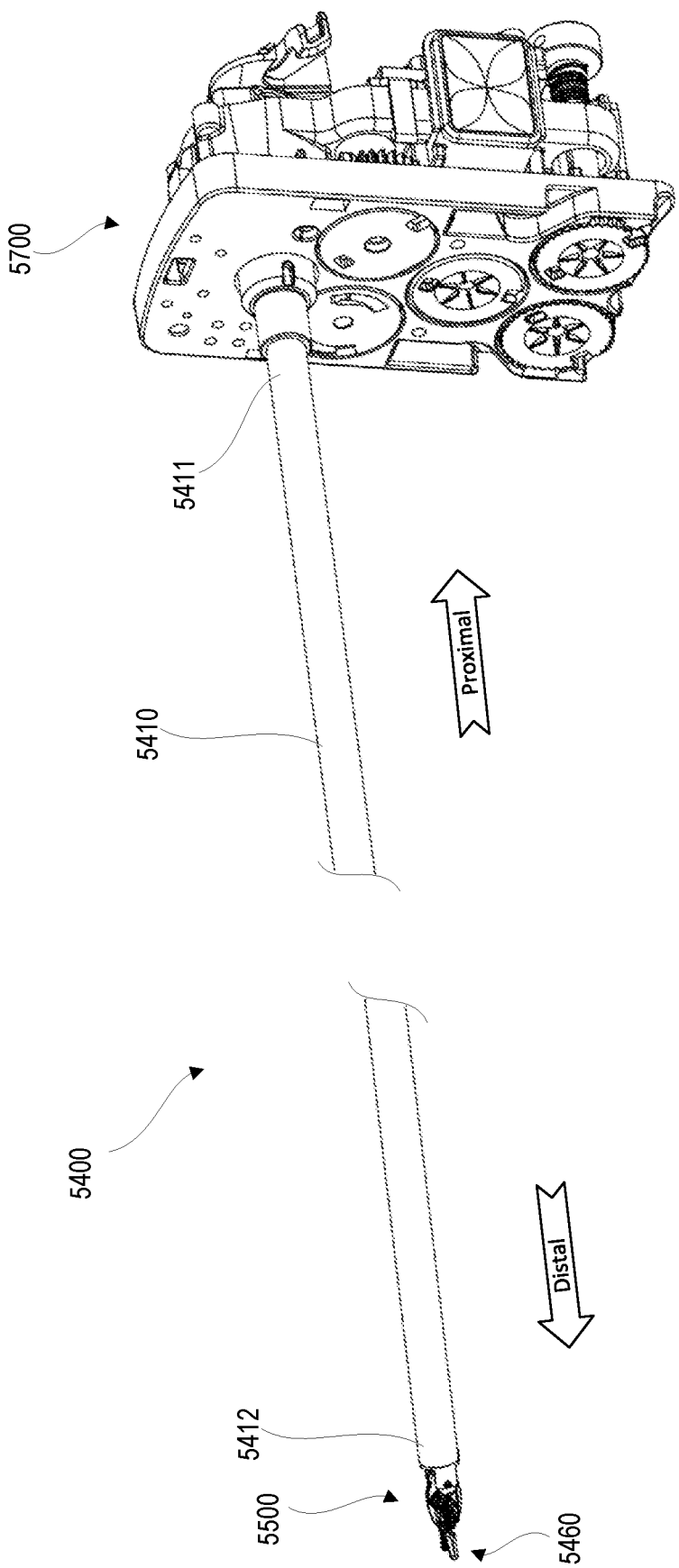
FIG. 13 is a perspective view of a medical device, according to an embodiment.
Figure 14:
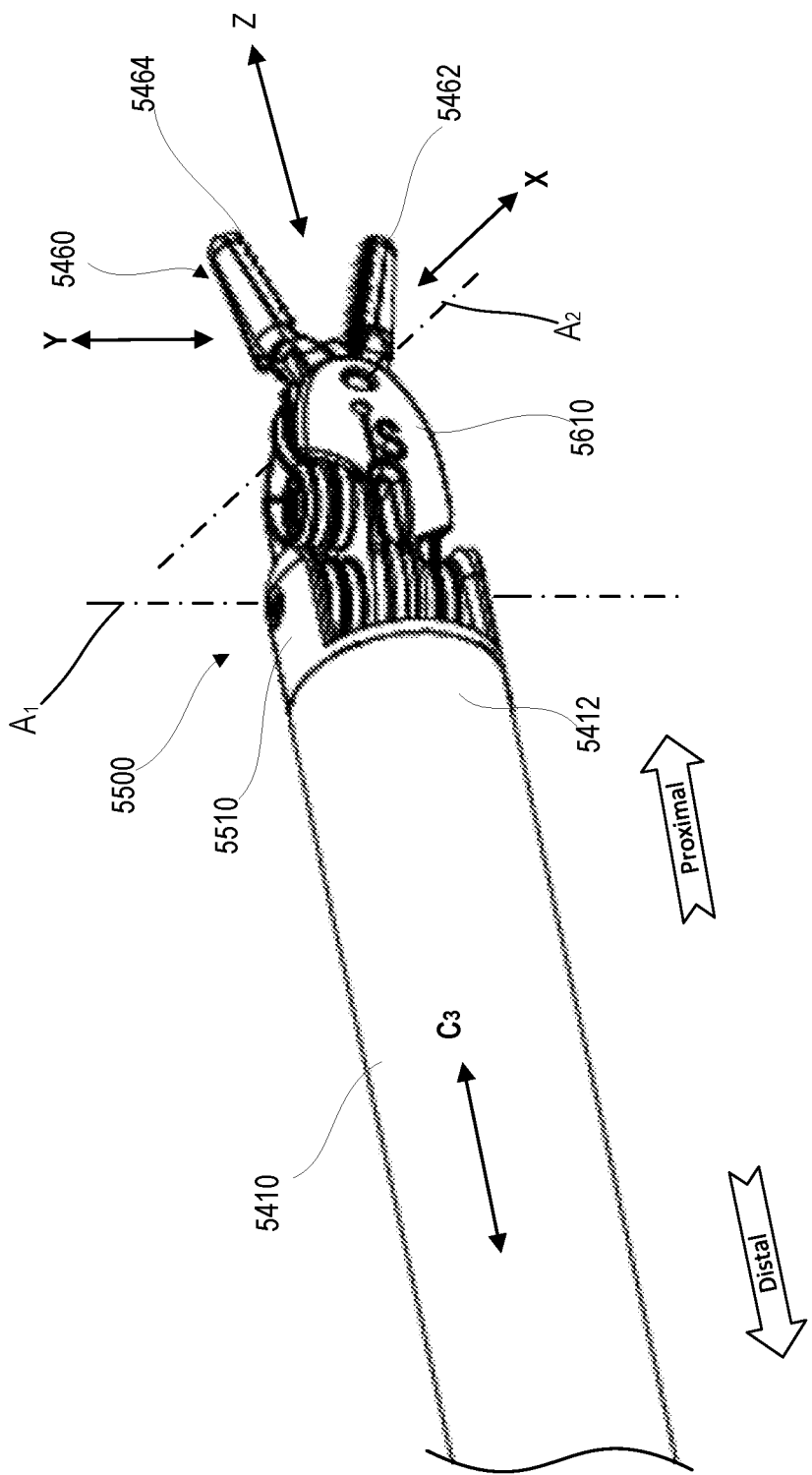
FIG. 14 is an enlarged perspective view of a distal end portion of the medical device of FIG. 13.
Figure 15:
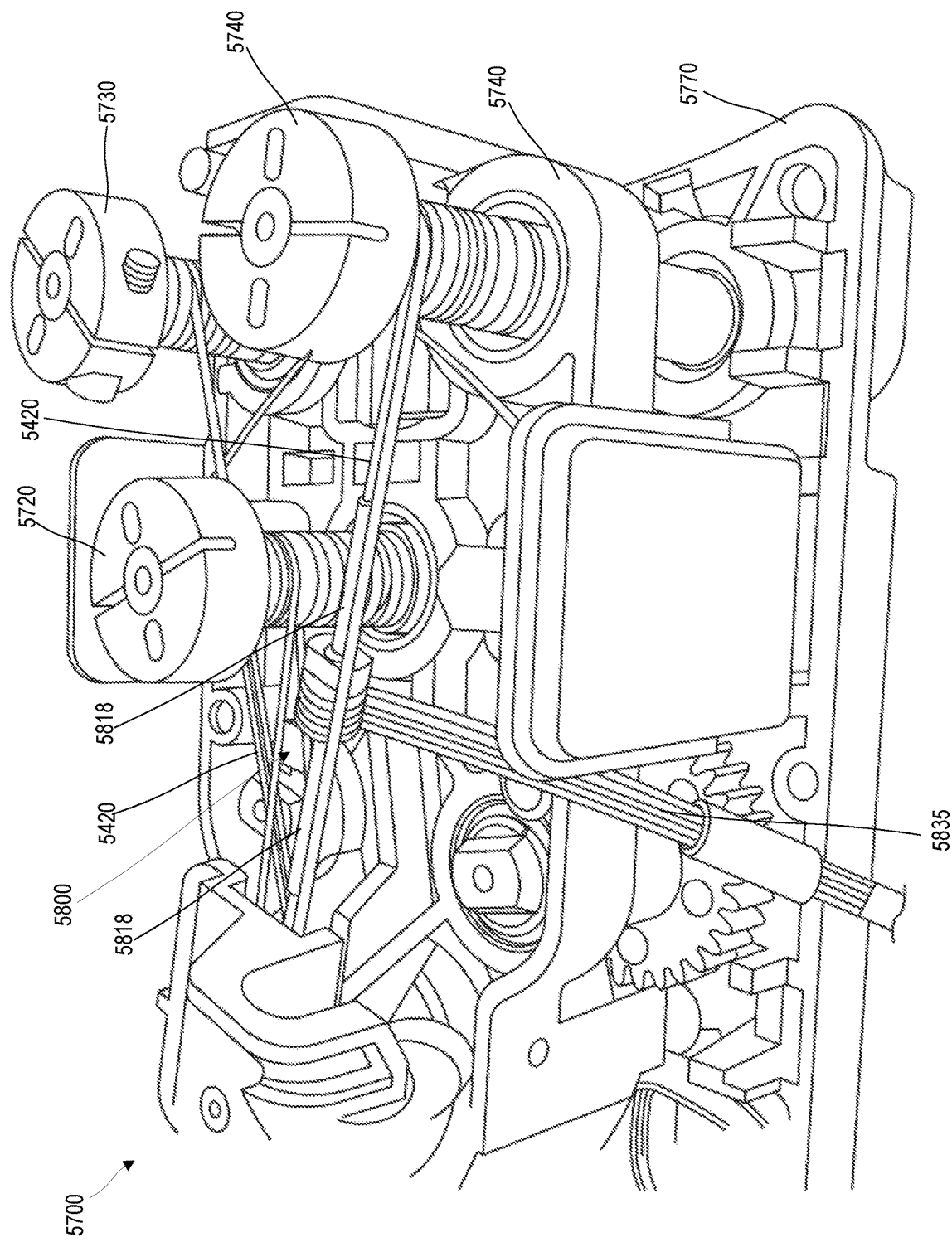
FIG. 15 is an enlarged view of a portion of the proximal mechanical structure of the medical device of FIG. 13, with some components removed or rearranged for illustration purposes.
Figure 16B:
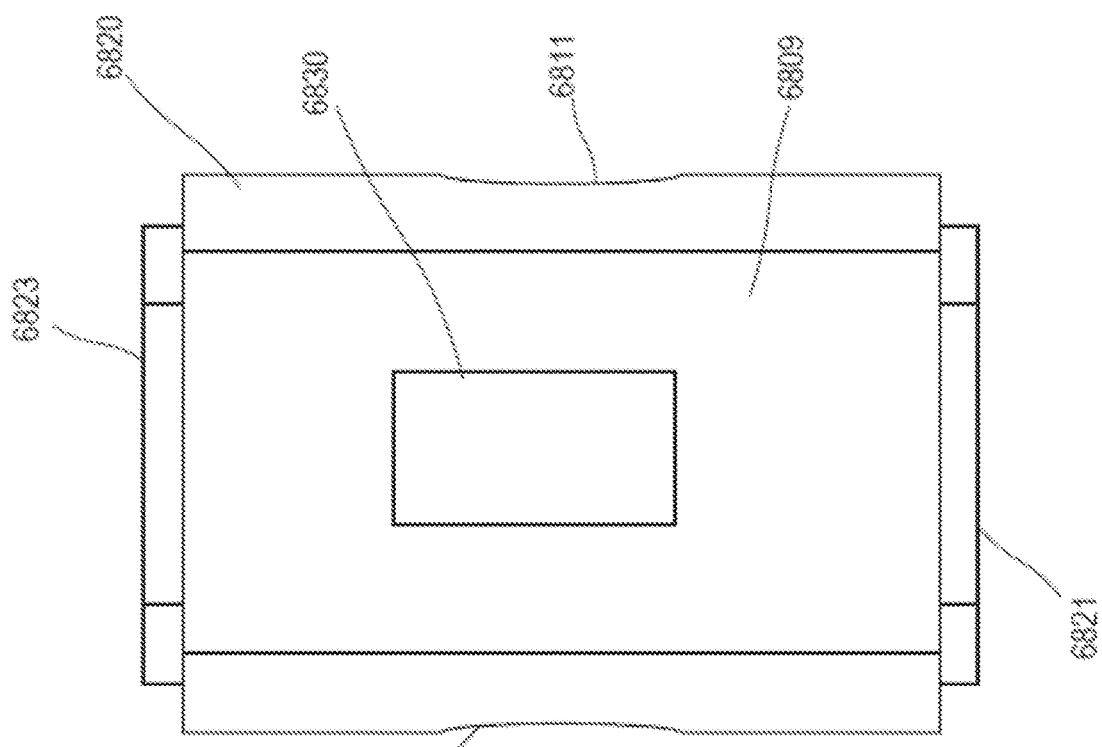
FIG. 16B is side view of the body of the force sensor unit of FIG. 16A.
Figure 16A:
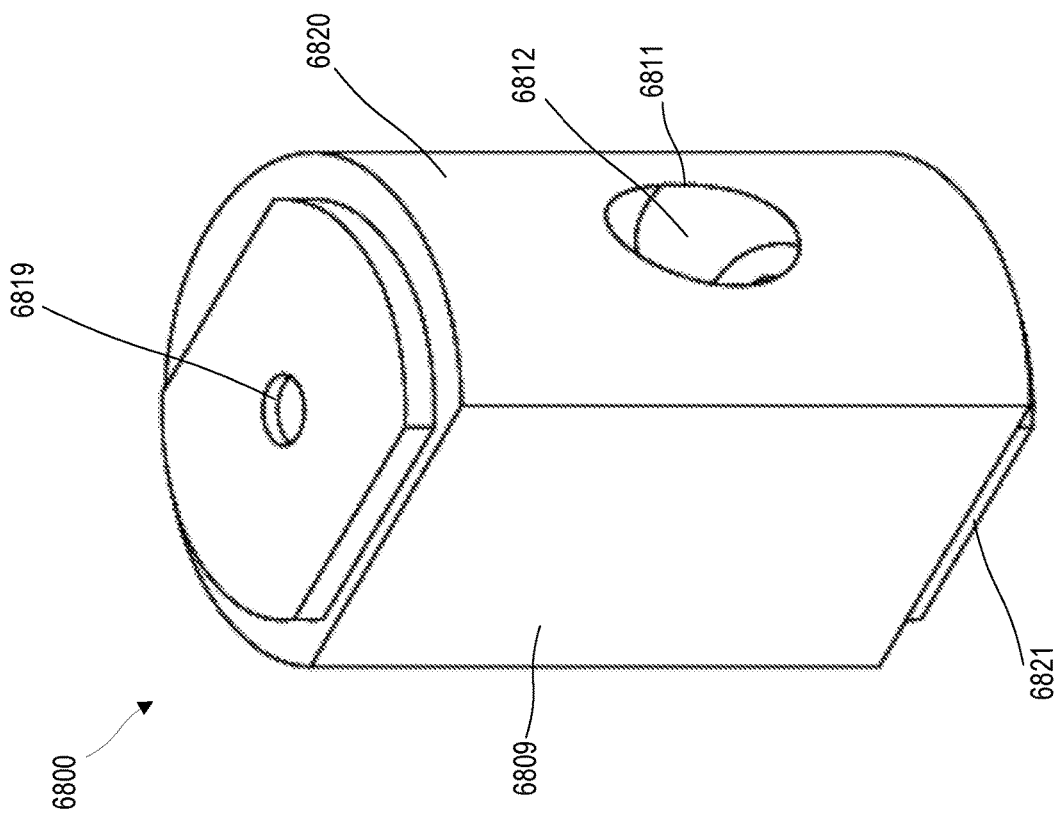
FIG. 16A is a perspective view of a body of a force sensor unit according to an embodiment.

FIGS. 13-15 are various views of the medical device 5400 and its components, according to an embodiment. As described above, the medical device 5400 can include the force sensor unit 5800 described with reference to FIGS. 10A-12 (or any of the other force sensor units described herein). In some embodiments, the medical device 5400 or any of the components therein are optionally parts of a surgical system that performs surgical procedures, and which can include a manipulator unit, a series of kinematic linkages, a series of cannulas, or the like. The medical device 5400 (and any of the instruments described herein) can be used in any suitable surgical system, such as the MIRS system 1000 shown and described above. In this embodiment, the medical device 5400 includes a mechanical structure 5700 at a proximal end portion of the medical device 5400, a shaft 5410, and a distal end mechanism which includes a wrist assembly 5500, and an end effector 5460. The instrument 5400 also include one or more connectors 5420 (see e.g., FIG. 15) that couple the mechanical structure 5700 to the wrist assembly 5500 and end effector 5460, and function as connectors or tension members to actuate the end effector 5460. The connectors 5420 can be, for example, a cable, a band, a push-pull rod, or the like. The instrument 5400 is configured such that select movements of the connectors 5420 produces rotation of the wrist assembly 5500 (i.e., pitch rotation) about a first axis of rotation $A_1$ (see FIG. 14) (which functions as a pitch axis, the term pitch is arbitrary), yaw rotation of the end effector 5460 about a second axis of rotation $A_2$ (see FIG. 14) (which functions as the yaw axis, the term yaw is arbitrary), a cutting rotation of the tool members of the end effector 5460 about the second axis of rotation $A_2$, or any combination of these movements. Changing the pitch or yaw of the instrument 5400 can be performed by manipulating the connectors in a similar manner as described, for example, in U.S. Pat. No. 8,821, 480 B2 (filed Jul. 16, 2008), entitled "Four-Cable Wrist with Solid Surface Cable Channels," which is incorporated herein by reference in its entirety. Thus, the specific movement of each of the connectors to accomplish the desired motion is not described below.

In this embodiment, the shaft 5410 includes a proximal end 5411 that is coupled to the mechanical structure 5700, and a distal end 5412 (see FIG. 14) that is coupled to the wrist assembly 5500. The proximal end of the shaft 5410 is coupled to the mechanical structure 5700 in a manner that allows movement of the shaft 5410 along a center axis $C_3$ of the shaft 5410 (shown in FIG. 14) relative to the mechanical structure 5700. The shaft 5410 also defines a lumen (not shown) and/or multiple passageways through which the cables and other components (e.g., electrical wires, ground wires, or the like) can be routed from the mechanical structure 5700 to the wrist assembly 5500.

In some embodiments, the medical device 5400 can include an outer shaft (not shown) that can be any suitable elongated shaft that can be disposed over the shaft 5410 and includes a proximal end that can be coupled to the mechanical structure. The outer shaft can define a lumen between the proximal end and a distal end. In such an embodiment, the shaft 5410 can extend within the lumen of the outer shaft and can move relative to the outer shaft. For example, the shaft 5410 can rotate relative to the outer shaft and/or can translate longitudinally in a direction parallel to the center axis $C_3$ of the shaft 5410 (i.e., the Z-direction).

Referring to FIG. 14, the wrist assembly 5500 includes a proximal first link 5510 and a distal second link 5610. The first link 5510 includes a distal portion that is coupled to a proximal portion of the second ink 5610 at a joint such that the second link 5610 can rotate relative to the first link 5510 about a first axis of rotation $A_1$ (which functions as the pitch axis, the term pitch is arbitrary). The proximal first link 5510 includes a proximal portion that is coupled to the shaft 5410.

A distal end of the distal second link 5610 is coupled to the end effector 5460 such that the end effector 5460 can rotate about a second axis of rotation $A_2$ (see FIG. 14) (which functions as the yaw axis). The end effector 5460 includes a first tool member 5462 (e.g., jaw) and a second tool member 5464 (e.g., jaw) each configured to engage or manipulate a target tissue during a surgical procedure. For example, the tool members 5462 and 5464 can include an engagement surface that functions as a gripper, cutter, tissue manipulator, or the like. In other embodiments, the tool members 5462 and 5464 can be an energized tool member that is used for cauterization or electrosurgical procedures. The end effector 5460 is operatively coupled to the mechanical structure 5700 such that the tool members 5462, 5464 can be actuated to rotate relative to shaft 5410 about the first axis of rotation $A_1$ and can be opened and closed to grasp an object. In this manner, the tool members 5462, 5464 can be actuated to engage or manipulate a target tissue during a surgical procedure.

The mechanical structure 5700 includes components to produce movement of the connectors 5420 (see FIG. 15) to produce the desired movement (pitch, yaw, or grip) at the wrist assembly 5500. Specifically, the mechanical structure 5700 includes components and controls to move some of the connectors in a proximal direction (i.e., to pull in certain connectors) while simultaneously allowing the distal movement (i.e., releasing or "paying out") of other of the connectors in equal lengths. In this manner, the mechanical structure 5700 can maintain the desired tension within the connectors, and in some embodiments, can ensure that the lengths of the connectors are conserved (i.e., moved in equal amounts) during the entire range of motion of the wrist assembly 5500. In other embodiments, however, conservation of the lengths of the connectors is not required.

In some embodiments, the mechanical structure 5700 can include one or more mechanisms that produce translation (linear motion) of a portion of the connectors. Such a mechanisms can include, for example, a gimbal, a lever, or any other suitable mechanism to directly pull (or release) an end portion of any of the connectors. For example, in some embodiments, the mechanical structure 5700 can include any of the mechanical structures (referred to as backend assemblies or actuators) or components described in U.S. Patent Application Pub. No. US 20157/0047454 A1 (filed Aug. 15, 2014), entitled "Lever Actuated Gimbal Plate," or U.S. Pat. No. US 6,817,974 B2 (filed Jun. 28, 2001), entitled "Surgical Tool Having Positively Positionable Tendon-Actuated Multi-Disk Wrist Joint," each of which is incorporated herein by reference in its entirety.

As shown in FIG. 15, the mechanical structure 5700 includes three drive components 5720, 5730 and 5740 (which function as capstans or actuator input pieces). The drive components 5720, 5730, 5740 are motor-driven rollers that rotate or "wind" a portion of the connectors 5420 to produce the desired connector movement, and therefore the desired movement of the wrist assembly 5500 and end effector 5460. In some embodiments, the mechanical structure 5700 can be constructed the same as or similar to the mechanical structures (referred to as backend assemblies or actuators) or components therein described in U.S. Pat. No. US 9,204,923 B2 (filed Jul. 16, 2008), entitled "Medical Instrument Electronically Energized Using Drive Cables," which is incorporated herein by reference in its entirety. The mechanical structure 5700 also includes an instrument support structure that includes a base 5770 and an upper support plate 5762, and a circuit board 5765 (see FIG. 12). In other embodiments, various support structures optionally may be used, such as a chassis, a frame, a bed, a unitized surrounding outer body of the mechanical structure, and the like. As also shown in FIG. 15, the force sensor unit 5800 is disposed within the mechanical structure. Although one force sensor unit 5800 is shown in FIG. 15, in other embodiments, more than one force sensor unit 5800 can be incorporated. For example, it may be desirable to have a force sensor unit 5800 coupled to each connector 5420. Further, in some embodiments, a force sensor unit 5800 can be coupled to a connector 5420 outside of the proximal mechanical structure 5700, for example, at a location within the shaft 5410 between the mechanical structure 5700 and the end effector 5460.

During use of the medical device 5400, motion of the drive components 5720, 5730 and 5740 produces a tension force within the connectors 5420, and that tension force is associated with an end effector (or grip) force exerted by the end effector 5460. As described above, as the end effector 5460 grips an object, a force is imparted at the jaws of the end effector 5460, and that force is related to the tension force within the connectors 5420. The sensor 5830 of the force sensor unit 5820 can be used to measure the strain (e.g., tension force) on the connector 5420, which in turn can be correlated to the grip force imparted at the end effector 5460. As described above, with knowledge of the drive pulley diameter, tensions measured in the connector 5420 can be correlated to the torques at the end effector grips (e.g., jaws).

Although the force sensor unit 5800 allows the connector 5420 to pass therethrough in a manner such that the entire tension force within the connector 5420 is transmitted through the body 5820 and sensed by the sensor 5830 on the body 5820, in other embodiments, a force sensor unit can include other features or means to couple a cable to a force sensor unit to accurately measure the entire tension force within the cable. For example, FIGS. 16A-17B illustrate an alternative embodiment of a force sensor unit 6800. The force sensor unit 6800 can be used in a medical device, such as medical device 5400, as described herein, to measure a grip force at the end effector. The force sensor unit 6800 includes a body 6820 that has a first end 6821 and a second end 6823. A first internal channel 6812 and a second internal channel 6814 are each defined within the body 6820. The first internal channel 6812 extends between, and is in communication with, an opening 6811 through a side wall of the body 6820, and an opening 6813 at the first end 6821 of the body 6820. The second internal channel 6814 extends between, and is in communication with, an opening 6817 through a side wall of the body 6820 and an opening 6819 at the second end 6823 of the body 6820. As shown in FIG. 17B, the channels 6812 and 6814 are disposed at an angle relative to a longitudinal centerline of the body 6820 (i.e., the channels are non-parallel to the longitudinal centerline of the body 6820). A sensor 6830 (shown only in FIG. 16B) is coupled to an exterior surface 6809 of the body 6820. The sensor 6830 can be, for example, any type of force or pressure element such as a strain gauge (e.g., an electrically resistive strain gauge) or a piezoelectric or piezoresistive force sensing element (e.g., strain gauge or MEMS, etc.) as described above for previous embodiments.

In this embodiment, the body 6820 can be coupled to a connector (e.g., a cable, band, or the like (not shown)) that includes two portions with each having an end portion that is coupled to the body 6820. More specifically a first connector portion (not shown) can extend from an end effector (not shown), through the opening 6813 at the first end 6821 of the body 6820, and be secured within the first channel 6812. Similarly, a second connector portion (not shown) can extend from a drive component (not shown), through the opening 6819 at the second end 6823 of the body 6820 and be secured within the second channel 6814. The first connector portion and the second connector portion can be secured within the respective channels 6812, 6814 with, for example, a crimped end, knot, or fastener that can be positioned within the channels 6812, 6814 through the openings 6811 and 6817 and prevent the connector portions from being detached from the body 6820.

As described for previous embodiments, during use, the force sensor unit 6800 is coupled to each of the connector portions when the connector portions are in tension. The channels 6812 and 6814 are disposed at an angle relative to a direction of the tensile force on the connector. With the connector portions secured to the body 6820, the body 6820 can bear the full tensile force imparted to the connector portions. Thus in this embodiment, there is no need for a strain relief portion as described above for medical devices 4400 and 5400, and the sensor 6830 can accurately read the tensile forces being imparted on the connector portions.

Figure 18B:
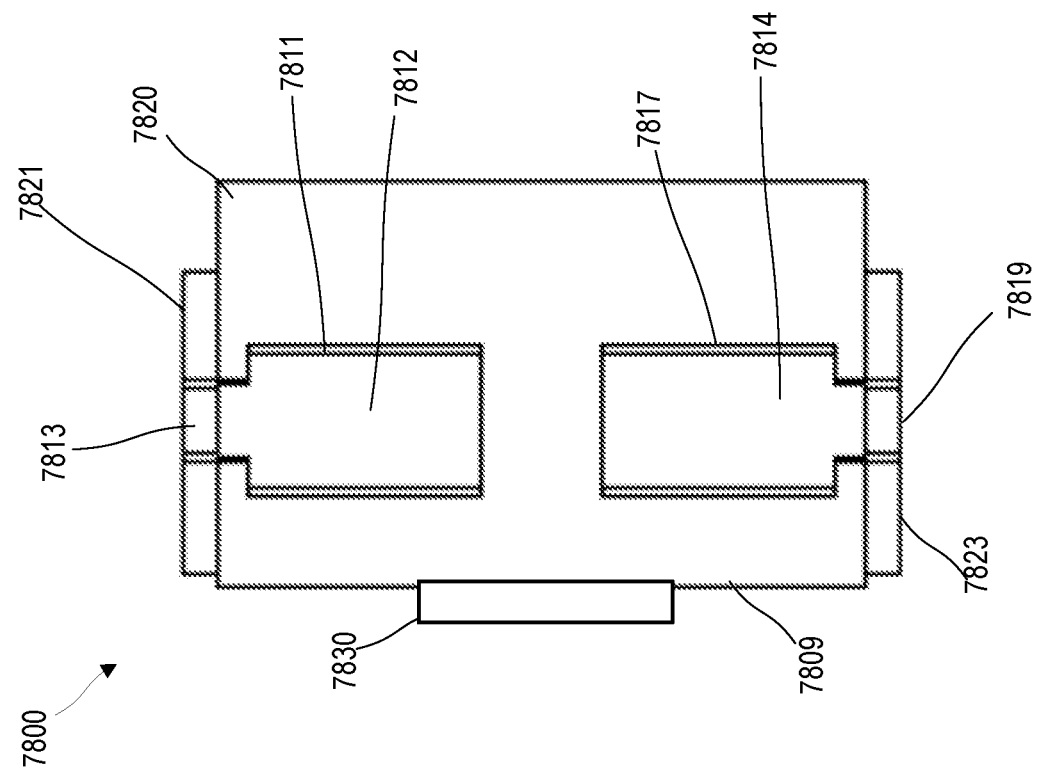
FIG. 18B is a side view of the body of the force sensor unit of FIG. 18A.
Figure 18A:
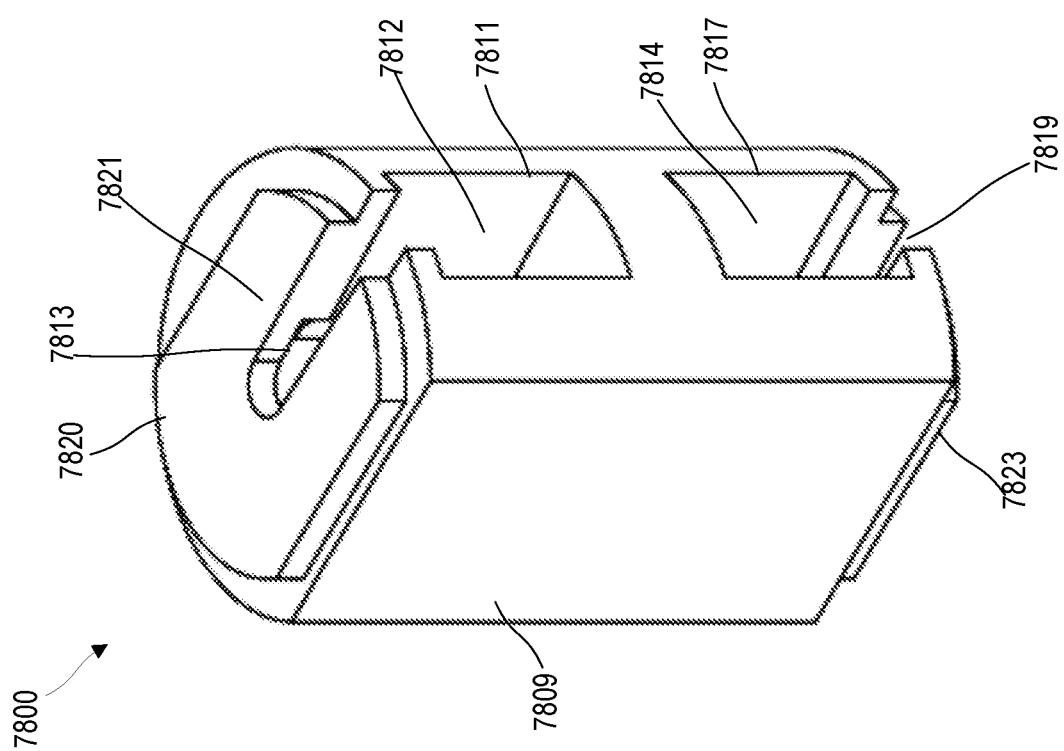
FIG. 18A is a perspective view of a body of a force sensor unit according to another embodiment.

FIGS. 18A-18B illustrate another alternative embodiment of a force sensor unit 7800. The force sensor unit 7800 can be used in a medical device, such as medical device 5400, as described herein, to measure a grip force at the end effector. The force sensor unit 7800 includes a body 7820 that has a first end 7821 and a second end 7823. A first internal channel 7812 and a second internal channel 7814 are each defined within the body 7820. The first internal channel 7812 extends between, and is in communication with, an opening 7811 through a side wall of the body 7820, and an opening 7813 at the first end 7821 of the body 7820. The second internal channel 7814 extends between, and is in communication with, an opening 7817 through a side wall of the body 7820 and an opening 7819 at the second end 7823 of the body 7820. As shown in FIGS. 18A and 18B, in this embodiment, the channels 7812 and 7814 are disposed vertically and parallel to a longitudinal centerline of the body 7820. A sensor 7830 (shown only in FIG. 17B) is coupled to an exterior surface 7809 of the body 7820. The sensor 7830 can be, for example, a strain gauge.

As with the previous embodiment, the body 7820 can be coupled to a connector (e.g., a cable, band, or the like (not shown)) that includes two portions, with each having an end portion that is coupled to the body 7820. More specifically a first connector portion (not shown) can extend from an end effector (not shown), through the opening 7813 at the first end 7821 of the body 7820, and be secured within the first channel 7812. Similarly, a second connector portion (not shown) can extend from a drive component (not shown), through the opening 7819 at the second end 7823 of the body 7820 and be secured within the second channel 7814. The first connector portion and the second connector portion can be secured within the respective channels 7812, 7814 with, for example, a crimped end, knot, or fastener that can be positioned within the channels 7812, 7814 through the openings 7811 and 7817 and prevent the connector from being detached from the body 7820.

As described for previous embodiments, during use, the force sensor unit 7800 is coupled to each of the connector portions when the connector portions are in tension. The channels 7812 and 7814 are disposed substantially parallel to a direction of the tensile force on the connector portions. With the connector portions secured to the body 7820, the body 7820 can bear the full tensile force imparted to the connector portions. Thus in this embodiment, there is no need for a strain relief portion as described above for medical devices 4400 and 5400, and the sensor 7830 can accurately read the tensile forces being imparted on the connector portions.

Figure 19:
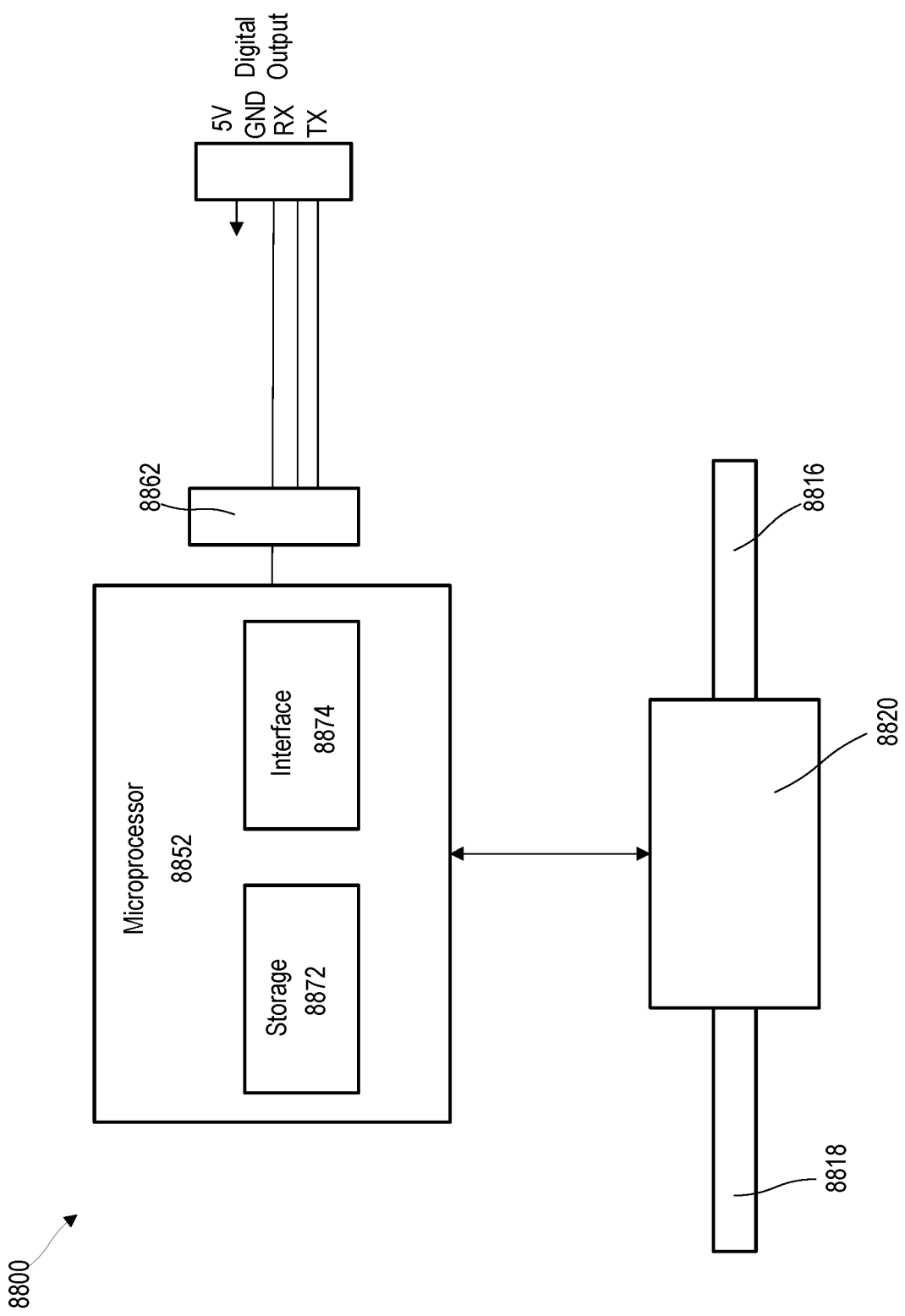
FIG. 19 is a schematic illustration of an embodiment of a force sensor unit.

FIG. 19 is a block diagram of a portion of a force sensor unit 8800 that can be implemented to measure grip force applied by the end effector of an instrument as described herein. Any of the force sensor units described herein can include the components described herein for force sensor unit 8800. Similarly, the force sensor unit 880 can include any of the components described above for previous embodiments of a force sensor unit (e.g., 4800, 5800, 6800. 7800) For example, the force sensor unit 8800 can be constructed similar to or the same as the force sensor units 4800 or 5800 and include a body 8820, a first tube 8816 and a second tube 8818 each coupled to the body 8820. The body 8820 defines a channel and each of the first and second tubes 8816 and 8818 each define a channel in communication with the channel of the body 8820. The forces sensor unit 8800 can be coupled to a drive connector (e.g. cable) of an instrument within the proximal mechanical structure of the instrument, such that the connector extends through the channels. In other embodiments, the force sensor unit 880 can be constructed in the same or similar manner as the force sensor units 6800 or 7800.

The force sensor unit 8800 can include or be coupled to a microprocessor 8852 that can include or have access to storage device 8872, such as an EEPROM. The force sensor unit 8800 can include other components, such as, for example, a microprocessor 8852 that can include an interface component 8874 such as a Universal Asynchronous Receiver/Transmitter (UART) or other communication interface to transmit (TX) a digital output and receive (RX) a digital signal. The received signal can be used to update calibration values in the storage device 8872 of the microprocessor 8852. Optionally, the force sensor unit 8800 can include a magnetic structure 8862 to help with electromagnetic interference (EMI) radiation reduction. The magnetic structure 8862 can be realized as a ferrite bead. Other magnetic material formats can be implemented for the magnetic structure 8862.

A machine-readable storage device may include any non-transitory mechanism for storing information in a form readable by a machine, for example, a computer or a microprocessor tasked to perform specific functions. For example, a machine-readable storage device may include read-only memory (ROM), random-access memory (RAM), magnetic disk storage media, optical storage media, flash-memory devices, and other storage devices and media. In various embodiments of a medical device with a force sensor unit described herein, a non-transitory machine-readable medium can comprise instructions, which when executed by a set of processors, can cause a system to perform various operations. The force sensor unit can comprise a microprocessor coupled to receive the first and second signals. In various embodiments, a non-transitory machine-readable medium can comprise instructions, which when executed by a set of processors cause a system to perform operations comprising methods of performing functions associated with the various embodiments described herein.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical assembly that performs minimally invasive surgical procedures, and which can include a manipulator unit, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the components of a surgical instrument as described herein can be constructed from any material, such as medical grade stainless steel, nickel alloys, titanium alloys or the like. Further, any of the links, tool members, beams, shafts, connectors, cables, or other components described herein can be constructed from multiple pieces that are later joined together. For example, in some embodiments, a link can be constructed by joining together separately constructed components. In other embodiments however, any of the links, tool members, beams, shafts, connectors, cables, or components described herein can be monolithically constructed.

Although the instruments are generally shown as having an axis of rotation of the tool members (e.g., axis $A_2$) that is normal to an axis of rotation of the wrist member (e.g., axis $A_1$), in other embodiments any of the instruments described herein can include a tool member axis of rotation that is offset from the axis of rotation of the wrist assembly by any suitable angle.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. A medical device, comprising:
an end effector, a mechanical structure, a connector, and a force sensor unit;
wherein the mechanical structure comprises a drive component;
wherein the connector extends from the drive component to the end effector, motion of the drive component produces a tension force within the connector, and the tension force is associated with an end effector force exerted by the end effector;
wherein the force sensor unit comprises a body, a first tube, a second tube, and a strain sensor coupled to the body of the force sensor unit;
wherein the body of the force sensor unit comprises a first end, a second end opposite from the first end, and a channel extending from the first end through the body to the second end;
wherein the first tube is coupled to the first end of the body of the force sensor unit, and the second tube is coupled to the second end of the body of the force sensor unit; and
wherein the connector comprises a first coupling portion, a second coupling portion, and a strain relief portion between the first coupling portion and the second coupling portion; and
wherein the first coupling portion of the connector is coupled to the force sensor unit within the first tube, the second coupling portion of the connector is coupled to the force sensor unit within the second tube, and the strain relief portion of the connector is in the channel of the body and is free of the tension force.

2. The medical device of claim 1, wherein:
the first tube is coupled to the first coupling portion of the connector with a first crimp, and the second tube is coupled to the second coupling portion of the connector with a second crimp.

3. The medical device of claim 1, wherein the strain sensor is a strain gauge.

4. The medical device of claim 1, wherein:
the strain sensor is coupled to an electrical wire, the strain sensor outputs via the electrical wire a signal associated with a strain produced by tension on the connector.

5. The medical device of claim 1, wherein the channel is surrounded by the body.

6. The medical device of claim 1, wherein the channel is C-shaped.

7. The medical device of claim 1, wherein:
the force sensor unit further comprises an electrical wire coupled to the strain sensor, the connector has a center line along a length of the connector, and the electrical wire is coupled to the body so that the electrical wire extends substantially parallel to the center line of the connector, and
the strain sensor outputs via the electrical wire a signal associated with a strain produced by tension on the connector.

8. A medical device, comprising:
an end effector, a mechanical structure, a connector, and a force sensor unit;
wherein the mechanical structure comprises a drive component;
wherein the connector extends from the drive component to the end effector, rotation of the drive component produces a tension force within the connector, and the tension force is associated with an end effector force exerted by the end effector;
means for coupling the force sensor unit to the connector;
means for providing strain relief to a portion of the connector; and
means for determining an amount of a force within the force sensor unit across the portion of the connector to which strain relief is provided.

9. The medical device of claim 8, wherein:
the means for determining the amount of the force across the portion of the connector comprises the force sensor unit;
the force sensor unit comprises a body, a first tube, a second tube, and a strain sensor coupled to the body of the force sensor unit; and
the body of the force sensor unit comprises a first end, a second end opposite from the first end, and a channel extending from the first end through the body to the second end.

10. The medical device of claim 9, wherein:
the connector comprises a first coupling portion and a second coupling portion; and
the means for coupling the force sensor unit to the connector includes a first crimp coupling between the first tube and the first coupling portion of the connector, and a second crimp coupling between the second tube and the second coupling portion of the connector.

11. The medical device of claim 9, wherein:
the means for providing strain relief to a portion of the connector includes the channel of the body of the force sensor unit, the channel comprises an inner diameter that is greater than a diameter of the connector so that the portion of the connector within the channel is free of the tension force.

12. The medical device of claim 9, wherein:
the strain sensor is coupled to an electrical wire, the strain sensor outputs via the electrical wire a signal associated with a strain produced by the tension force on the connector.

13. The medical device of claim 9, wherein the channel is surrounded by the body.

14. The medical device of claim 9, wherein the channel is C-shaped.

15. The medical device of claim 9, wherein:
the force sensor unit further comprises an electrical wire coupled to the strain sensor, the connector has a center line along a length of the connector, and the electrical wire is coupled to the body so that the electrical wire extends substantially parallel to the center line of the connector, and
the strain sensor outputs via the electrical wire a signal associated with a strain produced by the tension force on the connector.

16. A medical device, comprising:
an end effector, a mechanical structure, a connector, and a force sensor unit;
wherein the mechanical structure comprises a drive component, motion of the drive component produces a tension force within the connector, and the tension force is associated with an end effector force exerted by the end effector;
wherein the force sensor unit comprises a body and a strain sensor coupled to the body of the force sensor unit, a first channel within the body of the force sensor unit and a second channel within the body of the force sensor unit; and
wherein the connector comprises a first portion and a second portion, the first portion extends from the drive component to the body and is coupled to the body within the first channel, the second portion is coupled to the body within the second channel and extends from the body to the end effector.

17. The medical device of claim 16, wherein:
the body comprises a first opening and a second opening, the first opening in fluid communication with the first channel, the second opening in fluid communication with the second channel, an end of the first portion of the connector is received through the first opening and coupled to the body within the first opening, and an end of the second portion of the connector is received through the second opening and coupled to the body within the second channel.

18. The medical device of claim 16, wherein:
the strain sensor is coupled to an electrical wire, the strain sensor outputs via the electrical wire a signal associated with a strain produced by the tension force within the connector.

19. The medical device of claim 16, wherein:
the first channel is surrounded by a first portion of the body and the second channel is surrounded by a second portion of the body different than the first portion of the body.

20. The medical device of claim 16, wherein at least one of the first channel or the second channel is C-shaped.

21. The medical device of claim 16, wherein:
the force sensor unit further comprises an electrical wire coupled to the strain sensor, the connector has a center line along a length of the connector, and the electrical wire is coupled to the body so that the electrical wire extends substantially parallel to the center line of the connector, and
the strain sensor outputs via the electrical wire a signal associated with a strain produced by the tension force within the connector.

* * * * *